United States Patent
Anderson et al.

(10) Patent No.: US 7,968,124 B2
(45) Date of Patent: Jun. 28, 2011

(54) COMPOSITIONS FOR THE REVERSAL AND DETOXIFICATION OF ANESTHETICS AND OTHER COMPOUNDS AND METHODS OF THEIR USE

(75) Inventors: David M. Anderson, Ashland, VA (US); Vincent M. Conklin, Richmond, VA (US); Benjamin G. Cameransi, Georgetown, SC (US)

(73) Assignee: Lyotropic Therapeutics, Inc., Ashland, VA (US)

( * ) Notice: Subject to any disclaimer, the term of this patent is extended or adjusted under 35 U.S.C. 154(b) by 14 days.

(21) Appl. No.: 11/951,847

(22) Filed: Dec. 6, 2007

(65) Prior Publication Data

US 2008/0145434 A1    Jun. 19, 2008

Related U.S. Application Data

(63) Continuation-in-part of application No. 10/889,313, filed on Jul. 13, 2004, now Pat. No. 7,713,440.

(60) Provisional application No. 60/868,950, filed on Dec. 7, 2006.

(51) Int. Cl.
| | |
|---|---|
| *A61K 9/14* | (2006.01) |
| *A61K 31/05* | (2006.01) |
| *A61K 31/4164* | (2006.01) |
| *A61K 31/135* | (2006.01) |
| *A61K 31/505* | (2006.01) |
| *A61K 31/445* | (2006.01) |
| *A61K 31/045* | (2006.01) |
| *A61K 31/235* | (2006.01) |

(52) U.S. Cl. ........ 424/489; 514/731; 514/400; 514/647; 514/274; 514/330; 514/327; 514/338; 514/317; 514/626; 514/304; 514/458; 514/739; 514/762; 514/544

(58) Field of Classification Search .................. None
See application file for complete search history.

(56) References Cited

U.S. PATENT DOCUMENTS

| 5,922,317 A | * | 7/1999 | Kayar et al. ............... 424/93.4 |
| 2005/0101621 A1 | * | 5/2005 | Lipsky ......................... 514/282 |

FOREIGN PATENT DOCUMENTS

| WO | WO 01/22960 | * | 4/2001 |
| WO | WO 03/000236 | * | 1/2003 |
| WO | WO 03/106589 | * | 12/2003 |
| WO | WO 2005/034872 | * | 4/2005 |

* cited by examiner

*Primary Examiner* — Robert A Wax
*Assistant Examiner* — Suzanne Ziska
(74) *Attorney, Agent, or Firm* — Whitham Curtis Christofferson & Cook, PC

(57) ABSTRACT

Methods of attenuating the toxic or medically undesirable effects of drugs and toxins in a human by administering to a human an injectable formulation comprised of a dispersion of particles comprised of reversed cubic or reversed hexagonal lyotropic liquid crystalline material. The particles absorb or adsorb or otherwise sequester and attenuate the effect of drugs and toxins, and may be used as a rescue or reversal agent, or as a prophylaxis. The invention is especially applicable in reversing adverse effects of local anesthetics inadvertently delivered systemically, and attenuating the therapeutic effects of general anesthetics in the course of treatment.

17 Claims, No Drawings

COMPOSITIONS FOR THE REVERSAL AND DETOXIFICATION OF ANESTHETICS AND OTHER COMPOUNDS AND METHODS OF THEIR USE

This application is a continuation-in-part of U.S. patent application Ser. No. 10/889,313, filed Jul. 13, 2004, now U.S, Pat. No. 7,713,440 and the complete contents thereof is incorporated herein by reference. This application claims priority to U.S. Provisional Patent Application No. 60/868,950, filed Dec. 7, 2006, and the complete contents thereof is incorporated herein by reference.

BACKGROUND OF THE INVENTION

1. Field of the Invention

This invention focuses on the administration of dispersions of certain lyotropic liquid crystal compositions to attenuate the toxic or medically undesirable effect of one or more compounds present in the body of a human or other mammal. The particles in dispersion comprise reversed cubic phase and/or reversed hexagonal phase liquid crystalline material in which a toxin or a drug substance is soluble and partitions substantially. The particle dispersions are suitable for administration to a human, and are given preferably by injection, most preferably intravenously, in an amount sufficient to be effective in attenuating the effects of a toxin or therapeutic drug in the body. The attenuation of the effects of toxins or drug substances in the body may result from sequestering the toxin or therapeutic drug from the plasma, displacing the toxin from the site of action, inducing redistribution of the toxin, or by other mechanisms. Adjusting the composition by various means may increase or decrease the absorption or adsorption of a toxin or drug substance to the particles, the rate of uptake of the particles and associated toxins or drug substances by the liver, and otherwise impact attenuation of the effects of a toxin or drug substance. The invention is especially applicable in reversing adverse effects of local anesthetics delivered systemically, and attenuating the therapeutic effects of general anesthetics in the course of treatment.

2. Background of the Invention

In most clinical applications, local anesthetics are typically injected or applied at or near a site intended to render an area or region of the body insensate to painful stimuli. Once applied or administered, systemic absorption of the local anesthetic occurs or, in some instances, a portion of the injectate may be inadvertently administered directly into the vascular system. In any case, local anesthetics may exert varying degrees of systemic toxicity. Toxicity is usually directly proportional to the potency of the local anesthetic administered. It is widely believed that most local anesthetics exert their effects by binding to the alpha-subunit and blocking the voltage-gated sodium channel from an intracellular location, thereby conformationally inactivating the sodium channel and disrupting the influx of sodium ions preventing membrane depolarization. Local anesthetics are also known to block calcium, potassium and N-methyl-D-aspartate (NMDA) receptors to varying degrees. These differences are associated with the unique clinical profiles associated with each local anesthetic agent.

The unintentional intravascular administration of local anesthetics, bupivacaine in particular, which can occur during procedures designed to effect regional anesthesia can result in severe cardiac complications. These reactions include marked hypotension, atrioventricular dissociative heart block, idioventricular dysrhythmias as well as ventricular tachycardia and ventricular fibrillation. It is widely accepted that the R+ isomer of bupivacaine has a strong affinity to binding cardiac sodium channels and that its dissociation from this site is very slow. At higher concentrations, calcium and potassium channels can also be blocked, further exacerbating the cardiotoxic effects.

Bupivacaine induced cardiac toxicity is a life-threatening emergency in which aggressive measures must be undertaken to preserve life. These measures frequently involve immediate and repeated administration of vasopressors to maintain normovascular tone as well as other agents to control the bradycardia, complete heart block and the various cardiac dysrhytmias which ensue. Cardiopulmonary resuscitation may be required to maintain oxygenation of vital organs while the myocardium is in arrest. It is not uncommon to attempt to emergently effect extracorporeal oxygenation via cardiopulmonary bypass with membrane oxygenation (or similar device) to await the return of a normalized cardiac cycle once the offending concentration of bupivacaine has been redistributed, metabolized or otherwise inactivated, and allow for the physiologic normalization of the myocardial cycle.

A number of specific therapies for local anesthetic toxicity have been proposed over the years including bretylium, glucose/insulin/potassium infusions, emergent resuscitative efforts (i.e. cardiopulmonary resuscitation CPR), and cardiopulmonary bypass. Recently, attempts have been made to use fatty emulsions, typified by the product marketed under the name Intralipid®, to scavenge bupivacaine and thereby reverse toxic effects. [See, e.g., Weinburg G, Ripper R, Feinstein D L, Hoffman W. RA&PM 2003; 28:198; Weinberg et al. (1998) Anesthesiology 88(4):1071]. Similarly Intralipid® has been investigated for use in ropivacaine toxicity. [Litz et al. (2006) Anaesthesia 61:800]. Tebbutt et al. found increased survival in a rat model of verapamil toxicity. [Tebbutt et al., Acac. Emerg. Med. (2006) 13:134]. Bania, Chu and Stolbach looked at the use of Intralipid® to try to raise the LD50 in mice of an organophosphate compound, paraoxon. [Acad Emerg Med (2005) 12(5 Supplement 1): 12]. The group of Bania and Chu has also looked at the use of Intralipid® to treat toxicities from propanolol, VER, and amitriptyline. [Reported at the 2006 National SAEM Meeting, San Francisco Calif.]. Mathy-Hartert et al. investigated the use of Intralipid® against reactive oxygen species produced by phorbol myristate acetate, but found only a weak effect. [Mathy-Hartert et al., Mediators Inflamm. (1998) 7:327]. Microemulsions made from Pluronic surfactant, ethyl butyrate, fatty acid sodium salts and water have been proposed for scavenging bupivacaine by the group of Dennis et al. [See Dennis et al., U.S. patent application Ser. No. 10/420, 608, Varshney et al. (2004) J. Am. Chem. Soc. 126:5108 and Renehan et al. (2005) Reg. Anes. Pain Med. 30(4):380]. Dennis and coworkers have also proposed particles containing detoxifying enzymes, in U.S. Pat. No. 6,977,171.

Intralipid® and related parenteral fatty emulsions have several disadvantages and limitations in the present context. Perhaps most importantly, they rely on triglycerides (soybean oil in Intralipid®, other fats for the other fatty emulsions) for the solubilization and partitioning of compounds into the emulsion droplets, and as such they are strongly limited. Triglycerides are many-fold higher in molecular weight (on the order of 900 Da) than most compounds that are known to be effective solubilizers, as the favorable entropies of mixing associated with low-MW compounds is important for the functioning of most solvents. They are extremely hydrophobic, and thus very poor solvents for compounds that have one, or particularly more than one, polar group. Their propensity to support microbial contamination makes them poorly suited for field applications. And the high levels of polyunsaturated fats in lipid emulsions, combined with low levels of tocopherol to combat oxidation, lead to growing levels of peroxides and other free radical sources that can contribute to toxicities related to reactive oxygen species.

There is a need for a pharmaceutically acceptable composition and method for attenuating the effects of common drugs in circumstances in which they are toxic and in situations in which for other reasons, such as medical treatment or patient management, their attenuation is desirable which can work effectively, against a range of drugs and other toxins, and can be adjusted for different characteristics of action and different toxins.

SUMMARY OF THE INVENTION

In an exemplary embodiment of the invention, a method of attenuating the toxic effect of a toxin in a human or other mammal is achieved by administering to the human or other mammal in whom a toxin is or is suspected to be present an effective amount of a composition comprising particles which are formed from or include reversed cubic or reversed hexagonal phase material. The particles are preferably present in a stable dispersion which includes a liquid comprising a polar solvent. The particles may be ionically charged (anionic or cationic). The administration is preferably by injection (preferably i.v.) and results in the attenuation of the toxic effects of the toxin by the particles adsorbing or absorbing or otherwise sequestering the toxin from the site of toxic action.

It is another exemplary embodiment of this invention, a method of attenuating the therapeutic effect of a drug substance present in a human or other mammal is achieved by administering to the human or mammal in whom a drug substance is or is suspected to be present an effective amount of a composition comprising particles which are formed from or include reversed cubic or reversed hexagonal phase material. The particles are preferably present in a stable dispersion which includes a liquid comprising a polar solvent. The particles may be ionically charged (anionic or cationic). The administration is preferably by injection (preferably i.v.) and results in the attenuation of the therapeutic effects of the drug substance by the particles adsorbing or absorbing or otherwise sequestering the drug substance from the site of pharmacologic action.

A further exemplary embodiment of this invention is to provide a method of attenuating the effect of a chemical substance in a human comprising administering to the human a stabilized composition comprising lipid, tocopherol and a liquid comprising a polar solvent.

Whatever their specific therapeutic use, drugs are not always present at the most desired level in the body, and at times it may be necessary or beneficial to attenuate their effects. Some drugs of medical use, most notably the local anesthetics, can become life-threatening if they are inadvertently injected into a vein or artery, calling for removal or reduction to avoid or minimize neurotoxicity and cardiotoxicity. Other drugs used in medical practice, such as those associated with surgical procedures including general anesthetics like propofol and paralytic agents like vecuronium, can call for removal or reduction in a number of circumstances: for example, after interruption or even completion of a surgical procedure, it may be desirable to attenuate the lingering effects of the general anesthetic or paralytic agent whose normal therapeutic effect has become, post-operatively, a nuisance, danger or impediment to optimum patient management. In other cases, a drug may have side effects on account of generating toxic metabolites in circulation, it may be debilitating to the patient, or it may be detrimental in terms of tolerance or addiction, and attenuation of the effects of the drug may be an important therapeutic need. Certain compounds, such as cocaine or morphine, for example, are of course used in medical practice, but also are used as drugs of abuse and as such may require removal or reduction in the course of detoxification and rehabilitation. Furthermore, metabolites of certain drugs, such as cocaethylene in the case of cocaine and nor-meperedine in the case of meperedine (Demerol®), have considerable toxicity and their removal could be of importance in many settings. Finally, a toxin can be endogenous, such as an autoantibody or cortisol. In a particular embodiment of the invention, the invention permits attenuating the therapeutic effects of drugs on a selective basis, as well as in the removal of exogenous drug substances and endogenous toxins from the site of action.

Therapeutic agents such as propofol and other general anesthetics are selected for use and used, in part, on the basis of the duration and intensity of their therapeutic effect. In the course of their use, clinical circumstances may arise making it desirable to attenuate the therapeutic effects, for example, by reducing the time to emergence from the effect of a general anesthetic, or the duration of effect of the neuromuscular blocking agent. In an exemplary embodiment, the invention provides the ability to attenuate those effects and would provide an additional tool for optimum management of, for example, a course of surgery, as well as for the safety, comfort and convenience of the patient. In the case of an outpatient surgical procedure that proceeded successfully and more promptly than anticipated, for example, there may be benefits to patient and provider alike to accelerate the return of the patient to clear headedness, facilitating the discharge of the patient. In the case of a surgical procedure which has not proceeded according to plan and is being altered or terminated, there may be benefits to accelerating the patient's return to a state free from the therapeutic effects of a general anesthetic or a neuromuscular blocking agent.

In another setting, the course of delivering an anesthetic or securing an airway, it is of critical importance to relax skeletal muscles. This is most commonly accomplished with the use of neuromuscular blocking agents of either the depolarizing or non-depolarizing class. Neuromuscular blocking agents are used to facilitate endotracheal intubation in securing and maintaining a patent airway, effecting relaxation of skeletal muscles to enable certain operative procedures and to ensure patient safety in certain clinical settings. Depolarizing agents, i.e. succinylcholine, act as acetylcholine (Ach) receptor agonists and quickly cause short lived muscle relaxation due to the rapid diffusion away from the neuromuscular junction and are hydrolyzed by nonspecific cholinesterases. In contrast, non-depolarizing agents, i.e. vecuronium, function as competitive antagonists. The fact that non-depolarizers are neither metabolized by acetylcholinesterase nor eluted quickly from the Ach receptor predictably result in prolonged depolarization of the neuromuscular endplate, and yield longer duration of muscle relaxation. The best clinical practice and safest approach in the care of those paralyzed with neuromuscular blocker agents is to reverse, as completely as possible, the relaxant effects of these agents, especially non-depolarizing agents once relaxation is no longer required. Typically, reversal of the non-depolarizing agents is augmented by the administration of cholinesterase inhibitors, also known as anticholinesterases, i.e., neostigmine. These agents reversibly bind to the enzyme that degrades Ach thereby indirectly increasing the amount of Ach available to competitively displace non-depolarizing agents from the Ach receptor by re-establishing normal neuromuscular function at the neuromuscular endplate. Complications and other adverse reactions can occur with the administration cholinesterase inhibitors. These agents may be metabolized or administered in lower doses causing ineffective displacement of non-depolarizers from the receptor, yielding latent and unexpected return of paralysis. Administered in excessive doses, Achase inhibitors may paradoxically potentiate the effects of neuromuscular blockade. Other well known effects of increases in Ach associated with the use of Achase inhibitors include vagal mediated bradycardia, bronchospasm initiated by smooth muscle contraction, central nervous system effects including diffuse excitation, intestinal spasms, increased bladder tone and papillary constriction. Therefore, any strategy to minimize, supplement or preferably avoid the use of cholinesterase inhibitors in the reversal of neuromuscular blockade offers multiple advantages in the clinical setting. In an exemplary embodiment of the invention, this invention provides such a strategy.

Cyclodextrins are known to bind a number of drug molecules, such as rocuronium and vecuronium, and as such are being used as reversal agents for compounds like rocuronium. It should be noted that bradycardia is sometimes associated with the intravenous use of cyclodextrins, which is a distinct problem for the use of such compounds in connection with rescue from local anesthetic toxicity, where bradycardia is already a serious life-threatening complication. In another exemplary embodiment of the invention, an alternative to the use of cyclodextrins is provided.

Another embodiment of the invention relates to the management of the use of anesthetics in the clinical setting (e.g., hospital, doctor's office, clinic, nurses station, etc.). In practice, a patient will be provided with an anesthetic before, or after, or simultaneously with a composition containing particles that include reversed cubic phase or reverse hexagonal phase material. The patient will be subject to a medical or surgical procedure or will be simply observed. The anesthetizing effect of the anesthetic will be attenuated by the particles containing the reversed cubic phase or reverse hexagonal phase material. This allows control of the anesthetizing effect and may enhance a patient's recovery time. The type of anesthetics which may be managed in this way include both general anesthetics such as propofol, etomidate, ketamine, thiopental, a benzodiazepine, a barbiturate, an opioid, haloperidol, droperidol, and phencyclidine, and local anesthetics such as bupivacaine, lidocaine, ropivacaine, mepivacaine, and cocaine. With respect to general anesthetics, the invention can be used for decreasing a duration of sedation, reducing a time to emergence, reducing a duration of apnea, and reducing a time to full cognition.

In another embodiment of the invention, pharmaceuticals in a wide range of drug classes can have their effects selectively attenuated by providing the patient with a composition including particles that have either reversed cubic phase or reversed hexagonal phase materials. The methods of the invention can be used in conjunction with, for example, a patient that has or is suspected to have taken, or a patient that will be provided with a benzodiazepine, an opiate, a central venous system depressant, a respiratory depressant, a cardiovascular depressant, a psychomotor stimulant, a psychotropic, a sedative, a hypnotic, a muscle relaxant, and an organophosphate.

DETAILED DESCRIPTION OF THE PREFERRED EMBODIMENTS OF THE INVENTION

A. Definitions

"Attenuation" of a drug effect or toxic effect of a toxin means that one or more of the following occur (as compared to in the absence of treatment with the invention): substantial reduction in intensity of the effect, substantial reduction in the duration of the effect, substantial reduction in physiological insult and damage, substantially accelerated clearance of the drug or toxin from active or otherwise critical sites in the body, substantial reduction in symptoms of adverse reaction to the drug or toxin, substantial reduction in the concentrations of one or more toxic metabolites of the drug or toxin from critical sites in the body, or substantial reduction in pathological binding of exogenous or endogenous substance(s). In this definition, an effect, such as a reduction (e.g., in intensity), is considered substantial if it is clinically or medically useful or beneficial, or useful or beneficial in the management of a patient, to an extent that, in the view of one skilled in the art, it would warrant use of the invention in that situation. Also in the view of one skilled in the art, the effect of attenuating the drug or toxin should be preferential over other effects or side effects that would otherwise negate or render insignificant the desirable attenuating effect.

"Drug" means a compound consisting of or comprising an Active Pharmaceutical Ingredient (API).

"Toxin", in the context of this disclosure, is much broader than the connotation usually implied in day to day speech. In this disclosure "toxin" means any compound, or closely related group of compounds (such as different stereoisomers of a drug or different chain lengths of a particular lipid type), that pose a health risk or medical inconvenience to a mammal or human, and as such call for removal or reduction in the body, or for redistribution within the body (e.g., from tissues to blood, or from the blood to the liver, etc.). A toxin could be endogenous, such as an autoantibody or cortisol for example, though it will more often be an exogenous compound, and most typically an exogenous compound recognized to be toxic or antigenic at least under some circumstances (for purposes of this application, antigenic materials will be treated as toxins). Certain compounds, such as cocaine or morphine, for example, are of course used in medical practice, but also are used as drugs of abuse and as such may require removal or reduction in the course of detoxification and rehabilitation, and thus can be toxins in the context of this invention; furthermore, metabolites of such compounds, such as cocaethylene in the case of cocaine, have considerable toxicity and their removal by the present invention could be of importance in many settings. Other drugs of medical use, most notably the local anesthetics, can become life-threatening if they are inadvertently injected into a vein or artery, calling for removal or reduction, and in such cases become toxins in the context of this disclosure. Other drugs used in medical practice, such as those associated with anesthesia or pain control, including general anesthetics like propofol or paralytic agents like rocuronium or vecuronium, can call for removal or reduction in a number of circumstances, including overdosage, triggering of dangerous reactions such as malignant hyperthermia (MH) and respiratory depression. In addition, there are situations in which the treating physician or clinician may wish to attenuate the anesthetic effect for clinical reasons, for example, to allow a patient to be safely discharged from a hospital or clinic without having to wait for the entire length of time required for normal metabolism/excretion of the drug. Certain long-acting drugs of medical use, such as reserpine, or sustained-release formulations such as DepoMorphine, may call for removal or reduction if the duration of action needs to be cut, in which case the drug can be deemed a toxin in the context of this invention.

"Pharmaceutically-acceptable" generally designates compounds or compositions in which each excipient is approved by the Food and Drug Administration, or a similar body in another country, for use in a pharmaceutical or vaccine formulation, or belongs to a succinct class of compounds for which a Drug Master File is on file with a government regulatory agency, usually the FDA, or, less preferably, is known from extensive toxicity studies to be safe for the intended route of administration (which in the context of this invention is typically, though not always, intravenous). This also includes compounds that are major components of approved excipients. Listings of approved excipients, each with the various routes of administration for which they are approved, are published from time to time by the Division of Drug Information Resources of the FDA, as in January, 1996 and entitled "Inactive Ingredient Guide". The existence of a Drug Master File at the FDA is additional evidence that a given excipient is acceptable for pharmaceutical use, at least for certain routes of administration. For injectable products, a listing of approved excipients was published in 1997. See Nema, Washkuhn and Brendel (1997) PDA *J. of Pharm. Sci. & Technol.* 51(4):166. There are certain compounds, such as vitamins and amino acids, which are in injectable products (typically for parenteral nutrition) as "actives", and are thus known to be safe upon injection, and such compounds are considered herein as pharmaceutically-acceptable as excipients as well, for injection. There are also compounds which are not currently listed as an approved excipient, but which have been the subject of an extensive toxicity review and have been shown to be of very low toxicity, and non-mutagenic, and which, upon application to the proper authorities for a specific application, may be approved. A formulation pharmaceutically-acceptable for injection must be sterile.

"Site of action of a toxin or drug" is defined herein to be a location, in molecular terms, where the toxin or drug manifests a clinically significant toxic or pharmacologic effect, which in the context of the invention is a harmful or otherwise undesirable effect motivating application of the invention. To be at the site of action in some cases may include being in the tissue, organ, blood and/or other body fluids. In some instances, the drug or toxin is in such proximity, at the level of molecular binding, to a molecular target as to be capable of exerting a toxic or pharmacologic effect at that moment in time, such as acting as agonist or antagonist at a receptor protein, or otherwise binding and affecting an enzyme, lipid, saccharide, lectin, nucleic acid, vitamin, metal ion, neurotransmitter, hormone, or other target. The site of action of a toxin or drug could itself be exogenous, such as in the case of an antibiotic or antifungal compound where the site of action is on or in a microbe, existing at the time within the body of a human "Recovery" of a toxin or drug by a multitude of particles means that the particles substantially (i.e., with clinically desirable effect) displace it from its site or sites of toxic or pharmacologic action, or prevent it from interacting with that site before it ever requires displacement through interactions between the particles and toxin or drug, including but not limited to adsorption or absorption of the toxin or drug by the particles. An example of recovery that is broadly illustrative is where a toxin molecule, existing at or in the vicinity of a receptor, enzyme, or other molecular target by virtue of interactions with the molecular target, is sequestered by a particle by virtue of interaction(s) with the particle (such as hydrophobic interaction), said toxin molecule therefore becoming less prone to interact with the molecular target due to its sequestration by the particle and, in some cases, by movement of the particle away from the molecular target with subsequent clearance of the toxin and/or particle-toxin combination.

"Reversed liquid crystalline phases" in the context of this disclosure includes reversed hexagonal phase and reversed cubic phase, which itself includes both reversed bicontinuous cubic phase and reversed discrete cubic phase. These phases are known in the art of surfactant self-association. All are understood to be as described in detail elsewhere (e.g. in U.S. Pat. No. 6,638,621, filed Jun. 13, 2002, the complete contents of which is herein incorporated by reference).

B. Structure of the Composition to be Administered

Reversed cubic and reversed hexagonal phase material particles have quite a distinct morphology and therefore characteristics in comparison with oil in water emulsions and liposomes. The following compares four different 200 nanometer diameter particles, each made of one of the four materials above. Particles are compared by morphology, phase, radius of monolayer curvature, specific surface area, hydrophobic volume fraction, farthest distance to polar or apolar domains, and loading capacity.

Reversed cubic phase material has an intricate long range nanometer-scale order, and may exist either in bulk material or particulate form. The fluid lipid bilayer is arranged with precise curvature in repeating cubic space groups, creating interlaced polar and apolar microdomains. It has a very high interfacial surface area. The radius of monolayer curvature of a typical cubic phase is on the order of 3 nanometers. The specific surface area is approximately 40 $m^2$/mL. The hydrophobic volume fraction approximates 50-75%. The farthest distance to a polar or apolar domain from any point in or on the particle is only 3 nanometers. A reversed cubic phase particle can carry hydrophobic, hydrophilic and amphiphilic compounds in hydrophilic domains, in hydrophobic domains, and straddling both types of domains.

Similarly, reversed hexagonal phase material also has an intricate long range nanometer-scale order, and may be bulk material or particulate form. It also consists of a fluid lipid layer arranged with precise curvature creating polar microdomains, but in contrast to reversed cubic phase material, the structural units are cylinders arranged in a repeating pattern conforming to a hexagonal space group. Reversed hexagonal phase material also has a high interfacial surface area, though not as high as the reversed cubic phase. The radius of monolayer curvature of a reversed hexagonal phase is on the order of approximately 1.5 nanometers. The specific surface area is about 25 $m^2$/mL and the hydrophobic volume fraction is roughly 80%. As in the reversed cubic phase particle, the farthest distance to a polar or apolar domain is approximately 3 nanometers from any point in or on the particle. The reversed hexagonal phase particle, like the reversed cubic phase particle, can carry hydrophobic, hydrophilic and amphiphilic compounds in hydrophilic domains, in hydrophobic domains, and straddling both types of domains.

By contrast, an oil-in-water emulsion, such as Intralipid®, has no long range nanometer-scale order. It consists of fat droplets of various sizes and shapes surrounded by a lipid-rich layer in an aqueous medium. A 200 nanometer emulsion oil droplet has the lowest interfacial surface area of all particles compared here. It is comprised of an oil-rich liquid phase surrounded by lipid-rich phase. For such an emulsion particle, the radius of monolayer curvature is 100 nanometers. The specific surface area is only 6 $m^2$/mL. The hydrophobic volume fraction is 95%, but the farthest distance to polar or apolar domain is 98 nanometers.

Liposomes, too, differ significantly in structure and characteristics from reversed cubic and reversed hexagonal phase material particles. As true of emulsions, liposomes have no long range nanometer scale order. They occur only in particulate form: the basic structure is one or more solid lipid (or less commonly, fluid) bilayers, generally spherical, encapsulating a large polar liquid phase (usually aqueous) compartment. Liposomes have a very low interfacial surface area. They are derived from lamellar phase material, with a liquid phase core. The radius of monolayer curvature of a 200 nanometer liposome is approximately 100 nanometers. The specific surface area is 12 $m^2$/mL. The hydrophobic volume fraction is a very small, e.g. 5%, and the farthest distance to polar or apolar domains, like the emulsion droplet, is very large, 96 nanometers.

Without wishing to be bound by theory, the reversal of toxin and drug effects by the invention can be at least partly, if not fully, understood as resulting directly from the action of the particles in absorbing toxin within the particle interior, or adsorbing toxin at the particle surface. The former, namely absorption, can occur by virtue of the ability of the liquid crystalline material to solubilize the toxin or drug (which is amply demonstrated by Example 7), whereas the latter, adsorption, can occur by virtue of particle surface charge, specific capture molecules (such as antibodies) at the surface, hydrophobic interaction, solubilization and partitioning of the toxin within a particle surface layer such as a PEG-rich layer, or a number of other interactions. It should be understood that there is a distinction between a particle surface layer, and a distinct surface phase. Once toxin molecules in the immediate vicinity of the particles are so taken up by the particles, then due to one or more equilibria between free toxin and tissue-bound toxin, tissue-bound toxin molecules may diffuse out of tissue to fill the void left by the departed, particle-sequestered toxin molecules, where they can be ab/adsorbed, and the cycle continues. A more complete description of the process would take into account particle uptake of protein-bound toxin, RES uptake of particles, and other effects, but in any case the key step in the process is absorption or adsorption of toxin by the particles. It is at that point that the particles provided to a human or other mammal patient according to the invention step in and manifest their effect on the pharmacokinetics of the toxin.

The preferred particle architecture is that of a charge-stabilized, uncoated particle, as specified in detail in U.S. patent application Ser. No. 10/889,313. The uncoated particle has the distinct advantage that no occlusive layer interferes with the direct absorption or adsorption of toxins from medium. Thus for example, in the case of a toxin that exhibits slow or limited diffusion across bilayers, lamellar coatings are advised against since they would interfere with the toxin-absorbing properties of the reversed liquid crystalline phase interior. Indeed, a bicontinuous reversed cubic phase in particular, when uncoated, has a microstructure that allows bilayer-impermeable toxins to migrate directly into its pore space, where the toxin can be effectively maintained there by some combination of permselectivity, hydrophobic interactions with the bilayer, electrostatic interactions with the bilayer, van der Waals forces, or interaction with interior components of the cubic phase. Other particle architectures are possible as well provided that a substantial portion of the particle is a reversed cubic or reversed hexagonal phase. Solid-coated particles are antithetical to the purpose of rapid toxin uptake and are thus inconsistent with the objects of the invention; this applies to both crystalline lamellar and solid (crystalline or amorphous) nonlamellar coatings. Preferably, most or nearly all of the particle is a reversed liquid crystalline phase, with reversed cubic being most preferred among these.

The reversed cubic or reversed hexagonal phase material in particulate form should be readily accessed by the diffusion of toxin molecules from a site in the body to the material when the particle is at the site. In particular, the particle should not be occluded by an impermeable coating. An impermeable coating would be one which is substantially crystalline (such as a lipid in the gel phase), or more generally in which the self-diffusion coefficient of the toxin within the coating is strongly reduced relative to the self-diffusion coefficient inside the liquid crystalline material; alternatively, the probe of permeability known as $py_{10}PC$ (chemical name 1-palmitoyl-2-[1'-pyrenedecanoyl] phosphatidylcholine) can be used, and we take impermeable to mean that the self-diffusion coefficient of $py_{10}PC$ in the coating material as measured by the fluorescence photobleaching recovery method as used by Vaz et al. is less than about 1 $micron^2$/sec. [See Vaz, W. L. C., Z. I. Derzko, and K. A. Jacobson (1982) Cell Surf Rev. 8:83-136]. In that publication, Vaz et al. showed that $py_{10}PC$ exhibits a high D in lipid bilayers above the gel to liquid crystalline temperature, and low D below this transition temperature when the bilayers are crystalline. The dividing point of 1 $micron^2$/sec for this system is broadly indicative of coating fluidity in coated particles generally. The uncoated particles disclosed in U.S. patent application Ser. No. 10/889,313 are clearly accessible, as are, quite generally, reversed cubic and reversed hexagonal phase particles coated with coatings that are in liquid or liquid crystalline phases at body temperature (37° C. for humans).

The ionically-charged (electrostatically-charged), bilayer-bound components discussed above, and described in detail in U.S. patent application Ser. No. 10/889,313 which is herein incorporated by reference may bind toxin or pharmacological substances via electrostatic interactions, free of an impermeable coating, or coating of any sort.

In many applications, uncoated particles, particularly uncoated ionically charged particles, may be preferred to particles having reversed cubic or reversed hexagonal phase materials that are coated with solid coatings, such as those described in U.S. Pat. Nos. 6,482,517 and 6,638,621 to Anderson.

Analysis of the toxins of focus in this disclosure reveals that most of them have at least one polar group on the molecule, and the vast majority have more than one polar group per molecule. In a 200 nm emulsion droplet within Intralipid®, for example, only a very small fraction of the droplet volume is within a typical molecular dimension, say 3 nanometers, of a strongly polar group of the phospholipid-triglyceride particle composition; by strongly polar group we mean a polar group that is, for example, operative as a surfactant head group as discussed in, e.g., U.S. Pat. No. 6,638,621. By contrast, within a particle of the instant invention, virtually every point in the particle is within 3 nanometers of a polar group that is operative as a surfactant head group. Thus, even as hydrophobic groups of the toxin molecule localize in hydrophobic bilayer domains, any polar groups on the toxin can simultaneously localize in close proximity to such a surfactant polar group, and/or to water molecules (which hydrate the surfactant head groups), to experience energetically favorable polar interactions, without paying a large entropic price. This in turn leads to higher toxin solubilities, and higher partition coefficients, in particles of the instant invention over those of emulsion droplets, and this can translate directly into better performance of the instant invention over fat emulsions in terms of lower lipid doses (and thus less voluminous injections) required, and more rapid and complete removal of toxin from blood and/or tissue, and a wider range or toxins which can be effectively attenuated by treatment as described herein.

The surface area of accessible bilayer surface in a 200 nm particle of the bicontinuous cubic phase is an order of magnitude higher than that of an Intralipid® emulsion droplet of the same size. This in itself makes the dispersions of the invention advantageous over emulsions in a number of cases: where the toxin adsorbs to the bilayer or binds to a bilayer component; where the toxin binds to a component (such as an antibody) which extends from the bilayer surface, perhaps with a spacer arm; where uptake of the toxin is limited by diffusion through a concentration gradient that extends the full particle radius in the case of an emulsion droplet (thus approximately 100 nm), but only half the bilayer thickness in a cubic phase particle (thus approximately 2 nm); where the toxin is a macromolecule that binds to the particle by inserting a hydrophobic moiety (such as an alpha-helix) into the bilayer; and where the toxin has a low partition coefficient and remains in the aqueous domain but interacts sufficiently with the bilayer as to remain substantially within any aqueous pores of the particle. As an example of the first case listed, Example 12 provides an instance where the toxin, an earth metal ion, actually binds to the head groups of the phosphatidylcholine molecule itself.

Particle size for intravenous embodiments of the invention will preferably have an average particle size between about 80 and 1,000 nm, most preferably between about 100 and 700 nm, and wherein 90% of the particle volume is in particles with size less than about 1,500 nm and most preferably less than about 1,000 nm. The full particle size distribution can be adjusted by manipulating the processing conditions (in particular, homogenization time and temperature, and microfluidization if desired), in particular to adjust the fraction of particles that are below about 80 nm in size, since evidence indicates that such particles are cleared more slowly than particles above 80 nm, and it might be desirable in a particular application to have a longer-circulating fraction of particles, so that toxin removal continues for a longer period than in the absence of particles smaller than 80 nm.

Dispersions of uncoated particles of the preferred embodiment bind to plasma protein much less strongly than do emulsion droplets. This is important because where a large volume of emulsion droplets or particles of the invention are given for detoxification, it is disadvantageous, if not dangerous, for the particles or droplets to remove proteins and other components naturally present in the bloodstream. Moreover, in analogy with liposome-disrupting effects of protein opsonization well known in the art, overt uptake of proteins by lipid-based particles—particularly those such as emulsions which are already nonequilibrium structures—can rapidly destabilize particles. Because they are weakly attracted to plasma proteins, it is unlikely that a targeting or toxin-capturing compound associated with the particle will be interfered with by interaction of the particle and plasma protein.

C. Toxins Amenable to Attenuation by the Administration of the Composition of the Invention Toxins that are especially amenable to sequestration by particles of the instant invention are those that contain at least one hydrophobic group, and are thus considered either hydrophobic or amphiphilic. Compounds that are strictly hydrophilic, and contain no hydrophobic groups (compounds such as inorganic salts, glycine, and methanol), generally are not amenable to the invention since they will not partition preferentially into the particles of the invention. In the experience of the inventors, a compound is very likely to partition significantly into particles of the invention if one or more of the following criteria is met:

a) it has a contiguous string, or ring, of at least 6 carbon atoms in the molecule;
b) it has a solubility of at least 1% in alpha-tocopherol;
c) it has an octanol-water partition coefficient equal to or greater than about 100;
d) it lowers the surface tension of water to less than about 50 dynes/cm at low concentrations (e.g., less than 1%); or
e) if a peptide or protein, it contains a contiguous sequence of at least 4 hydrophobic amino acids.

Bupivacaine and many other local anesthetics clearly fit one or more of these criteria. For example, the octanol-water coefficient of bupivacaine at pH 7.4 is greater than 1,000. It should be noted that the reference to the traditional octanol-water partition coefficient ($K_{OW}$) is made here because this measure is often tabulated or otherwise available for a wide range of compounds. Nevertheless, in the context of this invention, it is the partition coefficient of the toxin in particles of the invention, as opposed to octanol, that is the most relevant measure. This disclosure will use the nomenclature $K_{QW}$ to indicate the partition coefficient in a cubic (Q) phase over water (or aqueous buffer more generally); that is, the ratio of concentration of the toxin in the cubic phase to the concentration in water, taken after the toxin has had time to equilibrate between contacting water and cubic phase volumes. It should be noted that this cubic phase-water partition coefficient, referred to in this paragraph, should be measured in the absence of albumin (unless the cubic phase in a particular formulation of the invention is, in fact, formulated with albumin as one ingredient) or other proteins. In the Examples below, a measurement is performed of partitioning into the cubic phase in the presence of albumin, in order to more closely mimic the situation where the invention is applied in the body, and this method of measurement is to be distinguished from measurement of the cubic phase-water partition coefficient per se. The term “effective partition coefficient” is used herein when the aqueous phase contains albumin, and typically this will be an albumin concentration of about 40 mg/mL.

In addition to these local anesthetics, propofol and other general anesthetics meet the above criteria. The invention could be used to attenuate the effects of the following intravenous general anesthetics, all of which have octanol-water partition coefficients greater than one hundred (100): eltanolone, minaxolone, methohexital, thiamylal, thiopental, ketamine, chlormethiazole, alphaxalone, and pentobarbital. As in the case of propofol, attenuation of these anesthetics by the invention could be performed either in cases of overdose, or simply to reverse anesthesia when it is no longer needed. Vecuronium bromide and other muscle relaxants also meet or more or these criteria (for example, by virtue of a steroidal backbone), and as shown in Example 15 below, although the octanol-water partition coefficient of vecuronium bromide is less than 100, its cubic phase-water partition coefficient is well above 100, and indeed above 1,000 for at least some cubic phases of use in the invention.

In addition to these drugs, other toxins that can be attenuated by the use of the instant invention include: (i) pharmaceutical compounds (some of which are also substances of abuse) such as propanolol, amitriptyline, verapamil, digoxin, reserpine, rocuronium, pancuronium, propofol, etomidate, halothane, enflurane, and methoxyflurane, benzodiazepines, N-methyl-3,4-methylenedioxyamphetamine, paracetamol, vitamin K antagonists (warfarin, acenocoumarol, phenindione), opioids (morphine, codeine, methadone, thebaine, heroin, oxycodone, hydrocodone, dihydrocodeine, hydromorphone, oxymorphone, nicomorphine), Clozapine, Risperidone and Olanzapine (antipsychotics), Paroxetine (antidepressant), Infliximab and Etanercept (anti-rheumatics), Paclitaxel (antineoplastic), Interferon beta (immunomodulator), phenylheptylamines, piperanilides, phenylpiperidines, diphenylpropylamine derivatives, benzomorphan derivatives, oripavine derivatives, and volatile anesthetics such as nitrous oxide, halothane, enflurane, isoflurane, sevoflurane, and desflurane; (ii) vitamins, particularly the fat-soluble vitamins; (iii) other drugs of abuse such as cocaine, heroin, LSD, "ecstasy", mescaline, amphetamines; (iv) compounds commonly known as poisons such as strychnine, carbon monoxide (a rather hydrophobic gas); (v) toxic compounds found in the environment such as pesticides, organophosphates, dichlorodiphenyltrichloroethane (DDT), morphinan derivatives, carbon tetrachloride, chloroform, trichloroethylene, tetrachloroethylene, dichloromethane, chlorofluorocarbons, benzene, toluene, xylene; (vi) toxins used in military and terrorist weapons such as VX; (vii) toxins from plant and animal sources such as snake venom, spider venom, insect toxins, ricin; allergens such as gluten, peanut oil; and (viii) substances of microbiological origin such as endotoxins, cholera toxin, *E. coli* enterotoxin, or indeed possibly even portions or whole bodies of viruses, prions, parasites, fungi, cryptosporidia, or even bacteria and other microorganisms. Lipopolysaccharide endotoxins such as Lipid A partition extremely strongly into lipid membranes such as those of the instant invention, and could be especially responsive to removal by the instant invention. The removal or attenuation of the effect of endotoxins in this manner could open up treatment to a variety of conditions, including, for example, sepsis.

D. Selection and Composition of Material Administered

As demonstrated below in Examples 17 and 18, the particle compositions can be used in vivo to recover diverse pharmacologic agents from their site of action or the blood stream to attenuate the effects of those agents. These results combined with Examples 1-16 and discussions herein, and particularly Example 7, suggest a wide variety of toxins would also be able to be recovered or captured in vivo using a particle composition which includes a reversed cubic phase or reversed hexagonal phase material.

In some specific applications the ability to adsorb, absorb, sequester or otherwise recover a pharmaceutical or toxin may be enhanced by choosing particles of specific constitutions. This may be accomplished by selection of a reversed liquid crystal composition that more favorably solubilizes the toxin or pharmaceutical of interest, and which is pharmaceutically-acceptable, and preferably which achieves a high partition coefficient over aqueous buffer at the relevant pH (typically about 7.4). Compositions for reversed liquid crystalline phases are discussed at length in U.S. Pat. No. 6,482,517, filed Sep. 8, 1998, U.S. patent application Ser. No. 09/994,937, filed Nov. 28, 2001, and U.S. patent application Ser. No. 10/460,659, filed Jun. 13, 2003, as well as U.S. patent application Ser. No. 10/889,313, the complete contents of all of which are herein incorporated by reference.

In summary, the liquid crystal composition should solubilize the toxin (or toxins), at a level that provides for clinically significant recovery of the toxin. Preferably the toxin is soluble in the reversed cubic or hexagonal phase liquid crystal to a level of at least 0.01%, more preferably equal to or greater than about 0.1%, and most preferably equal to or greater than about 1% by weight. The preferred solubility levels are reached by taking advantage of the inherent compound-solubilization properties of reversed liquid crystalline materials, discussed and demonstrated at length in the disclosures cited in the previous paragraph, and by further optimizing the liquid crystal composition through selection of the hydrophobe.

The reversed liquid crystal compositions typically are comprised of a lipid or surfactant, a hydrophobe and water. In the context of this invention, the term "hydrophobe" means the third major [pseudo-]component of a surfactant/water/third component liquid crystal composition even if this third component is, strictly speaking, amphiphilic by virtue of, e.g., a hydroxyl group, as in the case of linalool.

Liquid crystal compositions in which the main structural lipid (which is a surfactant, in accordance with the definition of the term "surfactant", see U.S. Pat. No. 6,482,517) is phosphatidylcholine ("PC"), or a phosphatidylcholine-rich product such as a purified lecithin, are strongly preferred in the invention. The current invention makes advantageous use of naturally-occurring phospholipids, particularly phosphatidylcholine, and most preferably phosphatidylcholine that have a transition temperature below body temperature, or preferably below ambient temperature—that is, the compositions employed are above the so-called Krafft line, temperatures below which crystalline phases appear and above which liquid crystalline and/or liquid phases appear. Phosphatidylcholine is put forth as uniquely well suited as the structural basis of injectable particles for toxin removal due to a constellation of favorable features, most importantly low toxicity, but including also the fact that it is endogenous, biocompatible, biodegradable, non-antigenic, cost-effective, and has a decades-long history of safe use in intravenous products at levels of 5-25 grams per day. While other surfactants and lipids, such as poloxamers (e.g., Pluronics), Tweens, cremophors, mono- and di-glycerides for example, can be used in the invention, these compounds must be scrutinized for toxicities that, in the context of toxin reversal, could lead to dangerous and unpredictable effects. This is particularly true since in the practice of this invention, in the face of toxic challenges to the body, fairly high volumes of the dispersions may be used, typically on the order of 100-400 mL, which contain on the order of 5-20 grams of lipid.

Most preferably, the hydrophobe for an injectable product will be one or more of the following five hydrophobes: tocopherol, linalool, squalene, benzyl benzoate, and long-chain diacetylated monoglycerides.

For an injectable product, in the most preferred method, the solubility of the toxin is first determined, using methods well known in the art, in each of the five preferred hydrophobes identified above. If desired, pairwise combinations of these five solvents (numbering ten) can also be tested, preferably at a 50:50 cosolvent ratio, still keeping the number of solubility tests to a manageable number (viz., 15). Generally speaking, for the purposes of this invention, the hydrophobe mixture that best solubilizes the toxin will also yield the liquid crystalline particle that exhibits the greatest partition coefficient (measured between the liquid crystal and water). Partitioning experiments can easily be performed by methods well known in the art, and as described in the Examples below. Based on these tests, and on the relative safety of these five hydrophobes themselves—or rather, on their history of safe use in the intended route of administration—a hydrophobe or hydrophobe mixture is selected. Tocopherol has the most extensive history of safe use particularly in intravenous products, as it has been used in parenteral nutrition for many decades, even in neonates, and thus it is the most preferred of the five hydrophobes from that perspective. Indeed, tocopherol is widely known to be of very low toxicity, with intravenous doses as high as 30 mg/Kg/day being essentially free from any adverse effects, and the excipient has a long history of safe use in intravenous products, both parenteral nutrition and in liposomal products. Diacetylated monoglycerides, in particular the brand Myvacet®, which has been used as an excipient in regulatory-approved intravenous products. Benzyl benzoate has been used in marketed injectable formulations, though not yet in intravenous formulations. Squalene has been used in vaccines as an adjuvant. Care should be taken to avoid inclusion of squalene in products intended for use in indications where adjuvant stimulation of the immune system may be contraindicated. Linalool has been found to be safe in a battery of toxicity studies and nonmutagenic [U.S. National Institute of Environmental Health Sciences report, Technical Resources International, Contract No. NO2-CB-50511, June 1997], but has not been used in marketed injectable formulations, and could be a candidate for formal approval in an appropriate product.

Tocopherol can be included as part of the hydrophobe mixture in most cases, for a number of reasons: it helps protect phospholipids from rancidification; it helps with the formation and stability of reversed cubic phases; it is a surprisingly effective solvent for a wide range of hydrophobic and amphiphilic compounds; and its cleansing effect as a vitamin is well known and can serve a helpful role in the detoxification applications of the invention. It should be noted that while wax-like components such as ethyl butyrate have been investigated for use in injectable products, neither ethyl butyrate nor any of the waxes are on the FDA Inactive Ingredient Guide as injectable excipients nor, of course, has any ever been used as a parenteral active or component, and the present invention avoids the use of these waxes.

Once the hydrophobe has been selected, the composition of the reversed liquid crystalline phase is then found by a simple phase behavior mapping, as described in, e.g., U.S. Pat. No. 6,638,821. Quantitative guidelines for determining the composition of a reversed cubic phase are given in U.S. patent application Ser. No. 10/460,659. An examination of viscosity and appearance under polarizing optical microscopy are indicative of the phases of lyotropic liquid and liquid crystal material.

A dispersant is typically, though not necessarily, incorporated in order to maintain the particles dispersed, and stable as such over time, preferably at least two years without detrimental increase in effective particle size, and in particular without an increase in the fraction of particles larger than about 1.5 micron (and more preferably 1 micron), as this fraction should preferably remain less than 10% preferably, and more preferably less than 1%, by volume. The term "dispersant" will be used herein even in cases where the compound only aids in maintaining stably dispersed particles, and relies on other co-dispersants for achieving the desired effect; for example, in a DMPG-containing dispersion of the invention, Myvacet (a long-chain diacetylated monoglyceride product from Kerry Bioscience) was necessary as co-dispersant. (DMPG is the abbreviation for dimyristoylphosphatidylglycerol). For most applications, the bile salts discussed herein are the preferred dispersants, with glycocholate being most preferred except possibly in situations where the danger posed by the toxin is low enough that a product with a high cost of materials, due to the high cost of glycocholate, is not justifiable. Bile salts are preferred for another reason, namely they promote uptake of particles by the liver, probably through binding of apolipoprotein E and/or related proteins, resulting in removal of the toxin from circulation; alternatively, cholesterol can be incorporated into the particles, and generally particles of the invention for intravenous use will contain either a bile salt or cholesterol, or both.

Other preferred dispersants are sodium oleate (preferably at 0.03% or less of the dispersion by weight), and other acidic diacyl phospholipids including phosphatidylglycerols, diphosphatidylinositol, and phosphatidic acid. For oral and topical products, other preferred dispersants are sodium docusate, and others given in U.S. patent application Ser. No. 10/889,313. For intravenous products with intended use in the United States, salts of fatty acids, including sodium oleate, should be avoided since they are not FDA approved as intravenous excipients, or in the case of caprylic acid, are approved only at extremely low levels, too low to be effective.

Preferred tonicity adjusters are neutral amino acids such as glycine or valine, and other standard, nonionic tonicity adjusters such as mannitol, glycerol, dextrose and xylitol.

E. Attenuation of Effect from Administration of Composition

The administration of an effective amount of the composition intravenously to a patient who is suffering neurotoxicity or cardiotoxicity due to the administration of a local anesthetic, as for example may occur from the inadvertent introduction directly into the bloodstream by injection of a toxic dose of the local anesthetic, would attenuate the severe neurological and cardiological toxicity caused by the local anesthetic. Administration of an effective amount of the composition under these circumstances would partially or entirely attenuate the toxicity, and mitigate or altogether end the toxic crisis for the patient.

The administration of an effective amount of the composition to a patient under the influence of a recently administered therapeutic dose of the general anesthetic propofol, would attenuate the effects of that drug, allowing the patient to emerge from anesthesia and return to clear headedness more quickly than without the administration of the composition. The ability to shorten the duration of effect can be of important medical value and become part of a standard of care from a point of view of safety and convenience. Similarly, the administration of an effective amount of the composition to a patient who has been treated with and is experiencing the therapeutic effects of a skeletal muscle relaxant such as vecuronium can attenuate the paralytic effects of that drug more quickly than in the absence of the administration of the composition. These and others can serve an important medical need in the surgical theater, and therefore facilitate safe use of optimal agents in these practices.

Prophylactic use of the invention is also possible. By administering an effective amount of the dispersion prior to or simultaneous with the anticipated ingestion, contact, or administration to a human of a drug or toxin, the effect of the toxin or drug can be attenuated from the beginning, and either mitigated in severity or duration or indeed attenuated to such an extent that clinical indications never appear. This is demonstrated in Example 16 below. Clearly, in order to successfully attenuate the effect of the toxin (since the definition of "attenuate" requires substantial reduction in the effect of the insult), the dispersion must be administered fairly close in proximity to the time of the insult, preferably less than about 15 minutes before the ingestion or administration of the toxin, and more preferably less than about 5 minutes. However, for purposes of prophylaxis, the invention encompasses embodiments that can circulate for considerably longer time periods than minutes. In particular, by the incorporation of "stealth" lipids known by those skilled in the art, circulation times may be greatly increased. Such lipids, which are readily incorporated into particles of focus in the invention as demonstrated in Example 9 below, include PEGylated lipids such as polyethyleneglycol-2000-phosphatidylethanolamine, Vitamin E TPGS, and other lipids created by covalent attachment of hydrophilic polymer chains to hydrophobic lipids. Settings where prophylaxis with the invention could be of medical importance include administration of local anesthetics at high-risk sites (guarding the patient against the toxic effect of a possible inadvertent injection into the blood stream), chemical or biological warfare arenas, clean-up operations at toxic waste sites, as well as other situations where exposure to toxins is probable or imminent.

The attenuation of a toxin by adsorbing or absorbing the toxin from the site of toxic action stands in contrast with other methods that rely on administering an antidote, provided that one is even available. While a competitive agonist or antagonist might preferentially displace a toxin from binding to a receptor or enzyme, the toxin can nonetheless remain at the site and continue to compete with the antidote for receptor binding, and in the case where the toxin and antidote bind to a common enzyme the competition continues as long as toxin remains in the organ of toxic insult, or in some cases as long as it remains in circulation. This is particularly problematic in cases where the toxin is only slowly detoxified by an organ such as the liver, and in such a case, the current invention provides for liver uptake and detoxification by virtue of liver uptake of the particles, which can easily be one, or two, or more, orders of magnitude faster than liver uptake of individual molecules; lipidic particles in the 80-1000 nm range can be substantially taken up by the liver in under 10 minutes. Thus, even in cases where a toxin can be displaced from a receptor, it can still be advantageous to administer dispersions of the current invention in order to clear the displaced toxin, provided it can be established that the dispersion does not clear the antidote preferentially over the toxin; this is unlikely if the effective partition coefficient into the particles as measured in the Examples herein is significantly higher for the toxin as compared to the antidote, and becomes more and more effective as an approach the more strongly the antidote binds to the receptor. In many cases, including the important case of bupivacaine, no specific antidote exists, particularly no drug that will effectively, rapidly and safely remove the toxin from its molecular target such as receptor or enzyme, and drugs that might be administered represent an attempt to counteract the toxic effect, such as the administration of vasopressin, epinephrine, norepinephrine, aminone, amiodarone, milrinone, lidocaine, calcium channel blockers, and phenyloin, none of which have been shown to be consistently safe and effective. [See Renehen E M et al. (2005) Reg. Anesth. Pain Med. 30(4):380]. The latter is not surprising because in the application of a non-displacing antidote (one that does not exhibit competitive inhibition of the toxin at the receptor site), the toxic effect of the toxin continues in parallel with the counter-effect of the antidote, and as such the antidote does not get to the root of the problem, of the toxic insult. Furthermore, with many toxins the receptor site may not even be known, and in such cases the current invention might be found to be effective in attenuating the toxic effects even in the absence of this knowledge. The invention could, in fact, be used to detoxify the body of a mammal thought, but not known, to be suffering the effects of a toxin or toxins, such as in cases in man where the patient might be unconscious, delusional, or unwilling to admit the ingestion of toxic substances such as drugs of abuse.

F. Varying the Composition

Other methodologies that fit within the spirit of the invention include the following. Targeting compounds, such as antibodies, lectins, ligands, bacterial adhesion receptors, complementary nucleic acids, bile salts, biotin derivatives, etc., can be incorporated (as described in U.S. patent application Ser. No. 10/889,313) so as to target particles of the invention to sites where toxins may accumulate and/or where they may do the most physiological damage, or to bind toxins directly, and/or to direct particles to elimination sites after toxin recovery. For example, a cholesterol- and/or bile salt-laden particle of the invention could be directed to, e.g., the liver by the ApoE mechanism discussed herein, where it could bring recovered toxin for detoxification, or where it could sequester toxin from the liver so as to, e.g., decrease the local concentration of free, unbound toxin. And glycolipid bacterial adhesion receptors, such as Forssman's antigen, are readily incorporated into the liquid crystalline particles of this invention, and such tagged particles could well bind bacteria with considerable specificity, so as to remove infectious bacteria, or to remove a bacterial by-product such as an endotoxin. Such capture could be coupled with proteases, nucleases, or antibiotics that could render the bound microbes noninfectious. Similarly, biospecific capture compounds, again including antibodies, lectins, ligands, complementary nucleic acids, bile salts, biotin derivatives, and also chelating agents, cyclodextrins, etc., can be incorporated into particles of the invention so as to amplify their ability to recover toxin.

Furthermore, the instant invention includes provisions for adjusting the rate of clearance, by the liver, of the particles, via a simple adjustment of the composition. The uptake of these toxin or drug-laden particles by the liver constitutes a dominant mechanism for the removal of toxin or drug away from tissues in the body where it exerts its pharmacological effect. Changing the dispersant from a bile salt, such as deoxycholate, to a charged phospholipid which is not recognized by Apolipoprotein E, can have a large effect on the circulation time of particles. Thus it is of significant importance that in the instant invention, the rate of clearance of the liquid crystalline particles can be increased by raising the concentration of cholesterol and/or bile salt in the particles, or decreased by lowering the concentration of these compounds. If a bile salt is used for this adjustment, it must satisfy two structural requirements: first, it must have a hydroxyl (—OH) group at the 3-position, and second, it must have an alkyl side chain at the C17 position of the steroidal ring system. Some of the preferred compounds for use in the instant invention, which satisfy these requirements, are the acid and salt (e.g., sodium salt) forms of cholic, glycocholic, deoxycholic, and chenodeoxycholic acids most preferably, and less preferably glycochenodeoxycholic, glycodeoxycholic, lithocholic, and ursodeoxycholic acids. Glycocholate and deoxycholate salts are especially preferred, as they are more hydrophobic, less toxic, and more reliably charged than others in the series. Deoxycholate has the additional advantage that it is inexpensive relative to glycocholate, although it is less reliably charged than glycocholate and the pH must remain above 7.2 to avoid precipitation.

In contrast, lipid emulsions such as Intralipid® are poorly suited for addition of bile salt or cholesterol without undue experimentation. Addition of bile salt to a fat emulsion tends to create mixed micelles, as is well known in the art. And while a small amount of cholesterol could, at least in principle, be incorporated in a fat emulsion, this would be difficult to prepare due to the extremely low aqueous solubility of cholesterol in water, precluding the possibility of mixing the fat emulsion with an aqueous cholesterol solution. More broadly, the natural instability of fat emulsion makes them extraordinarily sensitive to changes in composition.

Also, since reactive oxygen species (ROS) can be detoxified by virtue of the high tocopherol concentrations in the particles of the preferred embodiment, the invention could be useful in pre- or post-treatment of humans or mammals exposed to hazardous radiation. It should be noted that phosphatidylcholine is also reputed to aid in detoxification of ROS taken internally, and the preferred embodiment of the invention offers a combination of tocopherol and phosphatidylcholine. Furthermore, particles of the invention can reasonably be expected to perform better at detoxifying reactive oxygen species than solution formulations of vitamin E, for example, because the ability of the particles to sequester ROS compounds through the solubilization and partitioning effects discussed herein will translate into a longer residence time of proximity between the toxic compound and tocopherol (and phosphatidylcholine as well). Quite broadly, the sequestering effect of particles of the invention can be used to amplify the effect of detoxifying agents when those agents are embedded in the particles.

The toxin-attenuating aspect of the invention can be combined with other measures known in the medical arts to be of value in the treatment of the particular toxic insult. For example, particles of the invention, deliberately selected to attenuate the effects of a toxin A, could also be loaded with an Active Pharmaceutical Ingredient B, so as to deliver the agent B while at the same time substantially recovering toxin A. For measures that involve delivery of a pharmaceutical agent that is hydrophobic or amphiphilic in accordance with the discussions above, it must be borne in mind that this pharmaceutical agent may itself be significantly sequestered by particles of the invention if co-administered close in time. Thus it may be necessary to adjust dosages and dosing schedules of anesthetic agents, antibiotics, paralytic agents, and other agents used in the course of treatment when combined with treatment as per the instant invention.

G. Other Applications

As discussed above, the effects of anesthetics may be attenuated after performing a surgical procedure (e.g., elective or non-elective) or after an observation of a patient (e.g., simply observing a patients response to an anesthetic, etc.) by administration of a particles which include a reversed cubic phase or reversed cubic phase material. These methods can be applied to sequestering a wide variety of other drug substances and toxins. As discussed in more detail below, the methods may be employed in a number of other exemplary applications.

Decompression sickness, one instance of which is commonly called "the bends", is a condition in which nitrogen bubbles appear in the bloodstream and occurs in diving operations, pressurized mines, aircraft and spacecraft. Administration of dispersions of the invention, particularly embodiments in which fluorocarbons are incorporated, could substantially increase the solubility of nitrogen in the bloodstream by solubilizing diatomic nitrogen within the particle interior (that is, by absorbing nitrogen gas), and attenuate the noxious effects of nitrogen in decompression. This is an example of where a normally innocuous substance ($N_2$) can, under certain circumstances, become a toxin in the sense of this disclosure. While the authors are not aware of any published value for the octanol-water partition coefficient of diatomic nitrogen, its extremely low solubility in water (about 17.3 ppm at 25° C.) and its solubility in organic solvents indicates that Kow must be extremely high.

Similarly, carbon monoxide is sparingly soluble in water, but appreciably soluble in some organic solvents, again suggesting a high Kow, and thus the invention could potentially be used to attenuate the toxic effects of carbon monoxide poisoning. The effect of particles of the invention in sequestering carbon monoxide, particularly in a mammal already exposed to the toxin, might be further enhanced by incorporating hemoglobin or other heme-containing compound into the particles, and in contrast with red blood cells carrying heme-bound carbon monoxide, particles of the invention carrying CO would be rapidly cleared from the body.

A number of drugs are associated with QTc prolongation and/or torsade de pointes (TdP) including several that have been pulled off the market due to this toxicity problem, and the availability of a reversal agent such as provided by the instant invention could enable the safe use of these drugs. Some such drugs, potential toxins because of these effects, include disopyramide, procainamide, quinidine, amiodarone, bretylium, dofetilide, sotalol, astemizole, terfenadine, fluoroquinolone antibiotics such as grepafloxacin, levofloxacin, and sparfloxacin, macrolide antibiotics such as clarithromycin and erythromycin, imidazoline antifungals such as ketoconazole, antimalarials such as chloroquine, halofantrine and quinine, other antimicrobials such as cotrimoxazole, pentamidine and spiramycin, calcium antagonists such as prenylamine and terodiline, cisapride, and probucol, tricyclic and related antidepressant drugs such as amitriptyline, clomipramine, desipramine, doxepin, imipramine, maprotiline, nortriptyline, and antipsychotic drugs such as chlorpromazine, droperidol, thioridazine, ziprasidone, sertindole and pimozide.

High atomic weight earth metals, in particular strontium and barium, bind to phospholipid head groups, and have been found in the course of this work to bind rapidly and strongly to particles of the invention containing phospholipids (See Example 12). Thus the invention could be useful in removing such toxins from the body, pointing out yet another mechanism by which toxins can be bound by the invention. Similarly, the invention might be useful in removing leftover radioactive radionuclides following cancer therapy.

Bile salt accumulation in the blood causes jaundice, and since bile salts partition strongly into particles of the invention, another possible use for the invention is in the treatment of jaundice.

A number of compounds used in the operating room and emergency room are known to cause, in some people, allergic reactions such as anaphylaxis. Examples of such compounds, where the current invention could be used to remove such toxins, are salicylates, sulfonamides, cremophor, and penicillins, and to a lesser extent benzyl alcohol.

Due to the inclusion of significant levels of tocopherols in preferred embodiments of the invention, it is likely that the damaging effects of reactive oxygen species from a number of sources could be ameliorated with the invention. As discussed above, Intralipid® has been tested against reactive oxygen species from produced by phorbol myristate acetate, but only a weak effect was found, which is not surprising since Intralipid® does not contain significant levels of any strongly antioxidant compounds. In contrast, many preferred embodiments of the instant invention comprise both high levels of tocopherols and hydrophobic domains into which such species may preferentially partition, such domains typically being tocopherol-rich.

Ischemia and reperfusion are areas where the invention could be useful in a number of ways. The ability of tocopherol-containing embodiments of the invention to not only sequester, but also detoxify (by quenching radicals) reactive oxygen species is of course important in this potential application.

As another example, in organ transplants, the cardioplegia solution used to bring the heart to standstill (which typically includes local anesthetic among other toxins) can be mopped up with the methods and compositions of the invention administered, e.g., via the cardiotomy infusion site to deactivate the cardioplegia solution before attempting to restart the heart.

Injury also stems from biowaste in the donor organ from its prolonged lack of normal blood perfusion. These metabolites are "stunning" to the host upon reattachment of blood supply and the start of blood flow, and the current invention could be useful in removing these metabolites from the recipient's body.

In some embodiments of the instant invention, the reversed liquid crystalline phase material will contain, in its interior, a droplet of a hydrophobe-rich phase that is distinct from the reversed liquid crystalline phase; this is not to be confused with hydrophobic domains that are structural elements of the reversed liquid crystalline phase itself. This hydrophobe-rich droplet will be of a size between about 20 nm and 100 microns, that will contain as a major component a hydrophobe, thus a component of low solubility in water (less than about 3%), and/or of high octanol-water partition coefficient (Kow greater than or equal to about 10, more preferably greater than about 100), in which are solubilized the toxin and some fraction (perhaps very small) of each of the components of the second volume. The solubility of a given toxin in a mixture of hydrophobe and lipid is typically a very strongly increasing function of an increasing hydrophobe:lipid ratio, because the hydrophobe can generally be chosen specifically for its ability to solubilize the particular toxin whereas the choice of lipid has much more to do with its ability to form the desired liquid crystal (in the presence of the hydrophobe, in particular). Such "oil-core" reversed liquid crystalline particles are described in detail in U.S. Pat. No. 6,991,809, filed Jun. 21, 2002, the complete contents of which are incorporated herein by way of reference.

Besides intravenous injection, the preferred method for treating systemic toxicities of bupivacaine and other local anesthetics, and of general anesthetics quite broadly, the instant invention can be administered by a number of routes depending on the source and nature of the toxic challenge. Intraarticular injections could be particularly useful for insults within one or more joints of a mammal. Intramuscular, subcutaneous, and intraperitoneal administration may be used for insults that may be more local in nature. For example, if an intramuscular or subcutaneous administration of a drug has undesired consequences, local injection of dispersions of the invention could reverse, or at least attenuate, the undesirable effect. For additional attenuation, removal of the dispersed particles laden with toxin could possibly be effected, by, e.g., removing the particle-containing fluid from the site with a syringe, or by applying local pressure or suction, or by using the dispersion of particles more along the lines of an irrigation solution in the first place. For toxins taken in by mouth, the preferred route might be oral, e.g., via pills, tablets, lozenges, capsules, troches, syrups and suspensions, but most preferably as a simple dispersion in most cases. Intrarectal administration might also be useful for toxins within the GI tract. For toxic insults to the eye, particles and particularly dispersions of this invention can be applied through a wide range of ophthalmic routes: periocular, intraocular, conjunctival, subconjunctival, transconjunctival, peribulbar, retrobulbar, subtenons, transscleral, topical eye drop, topical gel, topical dispersion, intraorbital, intrascleral, intravitreal, subretinal, transretinal, choroidal, uveal, intracameral, transcorneal, intracorneal, and intralenticular. And for toxic insults which may be systemic but also may have a local aspect as well (e.g., for a snake bite where local concentrations at the bite site could be very high and yet systemic application of the particles is of course crucial as well), the invention can be applied through an appropriately chosen non-oral route including but not limited to intrathecal, intramuscular, subcutaneous, intra-arterial, rectal, intravaginal, intranasal, via inhalation, and topical. For those applications which are "local" in nature, i.e., administration of the dispersion is done in such a way that the dispersion is primarily confined to a local area where toxin is removed, it will in some cases be advantageous to remove, or otherwise displace, the dispersion from the local site so as to clear the toxin. This could be accomplished by one of a number of means, such as removal by a syringe (pulling the plunger back), flushing with an aqueous buffer or solution, removal by suction or blotting, etc.

It should be noted that, in the spirit of this invention, one can in principle envision the possibility of emulsion formulations that would utilize the more powerful solubilizers (i.e., the preferred hydrophobes) of the instant invention in place of the triglycerides of emulsions, such as the soybean oil of Intralipid®. However, to begin with, such systems would be inherently inferior to the particles of the instant invention, due to the very intimate association of polar (hydrophilic) and apolar (hydrophobic) groups in the reversed liquid crystalline phases which, as discussed above, quite generally results in higher solubilities and partition coefficients in reversed liquid crystalline phases, as compared to emulsions. Furthermore, and perhaps even more importantly, most, in fact nearly all, of the preferred hydrophobes in the instant invention are at least partially miscible with phosphatidylcholine (the overwhelmingly preferred surfactant), and thus form water-saturated reversed liquid crystalline phases when combined with PC and water—in sharp contrast with long-chain triglycerides, which due to near-complete immiscibility with PC form emulsions, rather than liquid crystals, at high water content.

EXAMPLES

The following Examples illustrate the present invention but are not to be construed as limiting the invention.

Example 1

An 800 mL batch of a dispersion of reversed cubic phase was prepared consisting of 862.83 mg/mL sterile water, 6.68 mg/mL sodium deoxycholate, 36.34 mg/mL alpha-tocopherol, 71.17 mg/mL PC-90G (Phospholipon 90G, from Phospholipid GmbH), and 22.98 mg/mL glycine. First, a 14% sodium deoxycholate solution was prepared by sonicating 5.6 g of sodium deoxycholate in 34.4 g of deionized water. An amount 38.62 g of this solution was stirred with 64.84 g of the phosphatidylcholine product Phospholipon PC-90G (from Phospholipid GmbH), and 16.55 g of alpha-tocopherol until well-mixed. This was slowly added to 480 gm of deionized water, and the mixture homogenized for three hours and then allowed to sit overnight without agitation. Later, the sample was re-homogenized for 2 hours and 200 g of a 9.2% glycine solution was subsequently added. The sample was homogenized for another hour and 14.55 g of alpha-tocopherol was added over 10 minutes. The dispersion was homogenized for another 2 hours followed by addition of 0.6016 g of sodium deoxycholate and homogenization for 1 hour. The resulting dispersion consisted of submicron particles of reversed cubic phase material, at a volume concentration of approximately 5%, with a strongly negative zeta potential to the bilayer surface (both internal and external surfaces within the particle), making it well suited for uptake of bupivacaine, or other positively-charged toxins such as vecuronium and morphine.

Example 2

Two dispersions per the instant invention were first prepared, varying in the composition of the hydrophobe, and then tested in the next Example for their ability to sequester bupivacaine, as compared to Intralipid® 20%. A 770 mL batch of a dispersion, hereafter called "RA5E", of the invention was prepared consisting of 937.38 mg/mL sterile water, 1.30 mg/mL sodium deoxycholate, 18.67 mg/l mL alpha-tocopherol, 21.85 mg/mL Phospholipon PC-90G, and 20.80 mg/mL glycine. 20.328 g of alpha-tocopherol and 23.802 g of PC-90G was stirred into 1.416 g of sodium deoxycholate dissolved in 14.520 g of sterile water. 42.7 g of this partial cubic phase was slowly added to 715.4 g of sterile water over 15 minutes. The mixture was homogenized at 5400 RPM for 5 hours to create a fine dispersion, followed by a 16.1 g addition of glycine. The dispersion was sparged, vialed and autoclaved.

In the second dispersion of this Example, hereinafter called "RA5EL", the hydrophobe in the reversed cubic phase consisted of a 50:50 mixture of alpha-tocopherol and linalool. In a 30 mL beaker, added 0.3236 grams of sodium deoxycholate, 2.6621 grams of a 50:50 mixture of alpha-tocopherol and linalool, 2.3052 grams of deionized water, and 2.6682 grams of the phosphatidylcholine-rich product Phospholipon 90 (from Phospholipid GmbH). This mixture was stirred until well-mixed. In a 25 mL graduated cylinder, 1.6085 grams of this mixture and 8.3992 grams of deionized water were combined, and this wash homogenized until it formed a fine dispersion, which was vialed and autoclaved at 121° C. for 15 minutes.

Example 3

In this Example the dispersions of Example 2 were tested for bupivacaine partitioning, as compared to Intralipid® 20%. A 50 mL solution of Krebbs-Ringer buffer was prepared with 4% albumin and approximately 0.1 mg/mL bupivacaine. In a 150 mL beaker, 2.0081 g bovine albumin was stirred until dissolved in 49.998 g Krebbs-Ringer buffer. In a separate 100 mL beaker, 50.0252 g of this Krebbs-Ringer Buffer with albumin was added to 0.0054 g of bupivacaine. 1 N HCl solution was added to the beaker until pH reached 2.0 and allowed to stir until bupivacaine dissolved. The pH was readjusted to 7.4 with 1 N NaOH solution.

One mL of formulation (RA5E, RA5EL, as prepared above, or Intralipid® 20%) was volumetrically added to a 15 cm length of 1,000 MW dialysis tubing wherein one end was tied shut. The bag was tied on the opposite ends and soaked in deionized water. The bag was then placed in a 10 mL graduated cylinders and 10 mL of Krebbs-Ringer buffer with 4% albumin and approximately 0.1 mg/mL bupivacaine was added volumetrically. The sample was allowed to sit without agitation until HPLC analysis was performed on the dialysis bath water.

In the following Table, the first number gives the percentage of total bupivacaine that was sequestered from the reservoir of spiked buffer; the second number gives the approximate amount sequestered per gram of lipid; this is a far more important measure; and the third number is the approximate effective partition coefficient between the lipid phase and the buffer:

| Dispersion | % of bupivacaine sequestered | Amount sequestered per gram lipid | Effective partition coefficient |
|---|---|---|---|
| Intralipid ® control | 11% | 0.5 mg/gm | 6 |
| RA5E from Ex. 2 | 25% | 3.7 mg/gm | 58 |
| RA5EL from Ex. 2 | 37% | 2.5 mg/gm | 46 |

Thus, the effective partition coefficient of bupivacaine (in the presence of albumin, hence "effective" partition coefficient) into particles of the instant invention was measured to be an order of magnitude higher than that into Intralipid® emulsion droplets.

Example 4

In this Example of the invention, the hydrophobe in the reversed cubic phase consisted of a 50:50 mixture of alpha-tocopherol and a diacetylated monoglyceride product marketed under the name Myvacet. A reversed cubic phase was prepared in a 12 mL test tube by combining 0.944 gm of Phospholipon 90 (Phospholipid GmbH, Cologne, Germany) along with 0.733 gm distilled water, and stirring until a homogenous consistency was reached. Then 0.272 gm Myvacet (Kerry Bio-Science, Norwich, N.Y.) and 0.273 gm of alpha-tocopherol (ADM) were added, and after thorough mixing the material was optically isotropic and of high viscosity, indeed a reversed cubic phase. This was then dispersed by homogenizing the liquid crystal in an aqueous solution of sodium deoxycholate, where the deoxycholate constituted 5% of the weight of the cubic phase, to create a dispersion of particles of the invention, which was then autoclaved. The Myvacet diacetylated monoglyceride behaves qualitatively very differently from long-chain triglycerides such as soybean oil when mixed with phosphatidylcholine and water: long-chain triglycerides are well known to form emulsions (Intralipid® being an instance), whereas this Example shows that diacetylated monoglycerides, with the right compositions, forms reversed liquid crystalline phases. Furthermore, diacetylated monoglycerides are far better solvents in general that long-chain triglycerides.

Example 5

In this Example, the hydrophobe in the reversed cubic phase consisted of a 50:50 mixture of alpha-tocopherol and benzyl benzoate. A reversed cubic phase was prepared in a 12 mL test tube by combining 0.950 gm of Phospholipon 90, along with 0.750 gm distilled water, and stirring until a homogenous consistency was reached. Then 0.276 gm benzyl benzoate (Sigma Chemical Company) and 0.285 gm of alpha-tocopherol were added, and after thorough mixing the material was optically isotropic and of high viscosity. This reversed cubic phase was then dispersed in a solution of sodium glycocholate, with the glycocholate being approximately 3.5% of the cubic phase by weight.

Example 6

In this Example, the partition coefficient of the compound methylene blue, an antimethemoglobinemic drug which is strongly colored, into particles of the invention was estimated using UV-Vis spectrometry. In a 10 mL syringe, 1 mL of an "RA5E" dispersion of the invention prepared as in Example 2 was spiked with 5 mL water and 250 microliters of a methylene blue solution. A small portion of this dispersion was passed through a 0.1 micron filter every 30 seconds until 6 minutes, then every minute until 12 minutes, and then every 2 minutes until 24 minutes. UV/Vis spectrophotometry was used to determine the concentration of methylene blue in samples collected at 1 minute and 22 minutes. The one-minute sample gave an absorbance of 1.15 and the 22-minute sample gave an absorbance of 1.26, these being equal to within the error of the experiment due to idiosyncrasies of the filtration step. UV/Vis analysis of the methylene blue stock solution compared with the methylene blue concentration in test tubes yielded a log $K_{QW}$>12 for the dispersion, and no significant difference of concentration or $K_{QW}$ at 1 minute and 22 minutes, where $K_{QW}$ stands for the partition coefficient measured between the cubic phase and water (or aqueous buffer).

Example 7

In this Example, selected drugs of considerable potency, and thus potential toxins, that are each of very low solubility in water and in soybean oil triglycerides (and thus in pharmaceutical emulsions such as Intralipid®) were tested for their solubilities in the preferred phosphatidylcholine/tocopherol/water cubic phase of the invention.

For a given compound X, the solubility in soy oil, and in tocopherol, was first determined as follows. Volatile organic solvents were first screened for the ability to dissolve both compound X and soy oil, or tocopherol. Methanol and dichloromethane were particularly effective for this purpose. After solubilizing the compound and soy oil or tocopherol together with the common solvent, the common solvent was then evaporated using a rotovap. At the resulting concentration of the compound in soy oil or tocopherol, the sample was monitored over approximately 4 weeks for any sign of precipitation, using centrifugation and microscopy; the microscopy was performed using a combination of Differential Interference Contrast (DIC), transmitted dark field, and polarizing modes. For the tocopherol cases, the solution of compound X in tocopherol was split into two parts, and phosphatidylcholine plus water added at the proper ratios to create a cubic phase (this composition is approximately 34% phosphatidylcholine, 31% tocopherol plus compound, and 35% water. This cubic phase was monitored for signs of crystallization of the compound. By repeating this process for a range of concentrations of compound X, the approximate solubility of the compound was determined to sufficient accuracy for the present purpose, in soy oil, tocopherol, and PC-tocopherol-water cubic phase. In the case of paclitaxel, the solubility was determined in both the PC-tocopherol-water cubic phase, and in another cubic phase with spearmint oil replacing tocopherol. The following table gives the final results of the work.

| Drug | Solubility (mg/mL) in: | | | |
|---|---|---|---|---|
| | soy oil | Water | tocopherol | cubic phase with tocopherol |
| Nimodipine | ~10 | 0.006 | 10 | 20 |
| Paclitaxel | <0.1 | 0.006 | 11/100* | 42* |
| Mycophenolate mofetil | 3 | 0.039 | 200 | 40 |
| Cyclosporin | 10 | 0.023 | 200 | 70 |
| Alphaxolone | <1 | <0.005 | 120‡ | 42‡ |
| Etomidate | 80 | 0.000045 | 200 | 105 |
| Hydrocortisone | <0.1 | 0.28 | 30 | 3 |
| Estradiol | spar. sol. | 0.05 | 10 | |
| Itraconazole | <0.5 | 0.000001 | 60 | 20 |
| Gluten | | <1 | | 25‡ |

*Spearmint oil used in place of tocopherol;
‡tocopherol mixed 50:50 with linalool.

The results in the table clearly demonstrate the power of the preferred cubic phase composition in solubilizing drugs and toxins, and its vast superiority over triglyceride-based emulsions in this representative selection of compounds.

Example 8

Reversed cubic phase material was prepared in a 250 mL beaker by combining 2.00 gm sodium deoxycholate (Marcor Development), 44.15 gm distilled water, 56.57 gm phosphatidylcholine 90G (Phospholipid GmbH), 15.70 gm linalool (Aldrich Chemical) and 20.39 gm vitamin E (Archer Daniels Midland). The mixture was stirred thoroughly after the addition of each component and the resulting material was optically isotropic and of high viscosity. Of this, 128.5 gm of cubic phase was added to a 3 L stainless steel beaker into which had previously been added 631.0 gm of distilled water. The cubic phase/aqueous solution was dispersed with a standard homogenizer (Silverson AX-60) at 5174 rpm for approximately two hours, then 40.0 gm mannitol (Sigma Chemical) was slowly added to the dispersion and homogenization continued for 15 minutes. The pH was measured at 7.6 (Hanna Instruments). A portion was filtered through a 5-micron Nylon® syringe filter and poured into 10 mL sterile Hollister-Stier glass vials. The vials were capped and autoclaved at 121° C. and 15 psi pressure for 20 minutes. After cooling, the zeta potential was measured at −58 mV (Beckman Coulter Delsa 440SX) and the particles were substantially submicron in size. The particle density in this formulation of the invention is approximately 16 vol %.

Example 9

This Example shows that particles of the instant invention can be produced which exhibit dramatically less plasma protein binding than emulsion droplets of the Intralipid® type. A dispersion of particles loaded with the drug propofol was first prepared as described in U.S. Ser. No. 10/889,313. Diprivan emulsion was obtained from the manufacturer. While these particles contain on the order of 10% propofol, the effect of the drug on protein binding is small compared to the effects of bile salts, surfactants, and cholesterol, as will be seen in the results below, so that the experiment is by and large a reasonable model of dispersions of the invention at least as far as plasma protein binding. A 10 microliter aliquot of dispersion, or emulsion, was diluted with 1000 microliters of deionized water, and also 30 microliters of human plasma was diluted with 3000 microliters of deionized water. In eight Nanosep Centrifugal devices with 300K MWCO, 200 microliters of dilute human plasma solution was incubated with 200 microliters of either a dispersion of the instant invention, or a marketed, Intralipid®-based propofol formulation. Centrifugal devices were spun down on a microcentrifuge for 20 minutes to separate unbound plasma proteins from particle-bound plasma proteins. SDS solution was added to particle-bound plasma proteins and heated in a boiling water bath for 1 hour. Then 50 microliters of each sample was loaded on gel electrophoresis with 950 microliters of Laemmli Sample Buffer. After performing SDS-PAGE, gels were fixed, stained, and destained according to standard electrophoresis procedure, and photographed, and contained ten lanes. Samples corresponding to the ten lanes are as follows, with all samples containing approximately 1% (10 mg/mL) propofol overall in the dispersion or emulsion (which would not be expected to qualitatively change the relative protein-binding properties of the dispersions or emulsions):

Lane 1: Long Range Protein Standard (control, i.e., no dispersion or emulsion involved);
Lane 2: Plasma proteins bound to Diprivan (marketed propofol emulsion, a 1% propofol in Intralipid® emulsion);
Lane 3: Plasma proteins bound to a dispersion of uncoated, reversed cubic phase particles containing propofol and stabilized with a bile salt;
Lane 4: Plasma proteins bound to a dispersion with DMPG (dimyristoylphosphatidylglycerol) and Myvacet® (a long-chain diacetylated monoglyceride) as dispersants;
Lane 5: Plasma proteins bound to a dispersion as in lane 3 but with 5% cholesterol incorporated in the particles;
Lane 6: Plasma proteins bound to a dispersion of phosphatidylcholine/tocopherol/propofol/water reversed cubic phase particles with 5% cholesterol in the cubic phase and Pluronic F-68 as dispersant;
Lane 7: Plasma proteins bound to a dispersion of phosphatidylcholine/tocopherol/propofol/water reversed cubic phase particles with Pluronic F-68 as dispersant (no cholesterol);
Lane 8: Plasma proteins bound to a dispersion of phosphatidylcholine/tocopherol/propofol/water reversed cubic phase particles with sodium oleate as dispersant, where the oleate concentration is quite low (0.03%);
Lane 9: Plasma proteins bound to Baxter's marketed 1% Propofol emulsion based on a fat emulsion;
Lane 10: Plasma proteins (control, i.e., no dispersion or emulsion involved).

Visual analysis of the stained electrophoresis gel showed that plasma protein binding of the 8 formulations (lanes 2-9) could be ranked from most to least binding as follows: lane 9>lane 2>>lane 8>>lane 6>lane 3>lane 4=lane 5>lane 7, with the last three showing almost no binding whatsoever.

It is clear from these data that emulsion droplets bound much more plasma protein than any of the dispersions of the instant invention. Furthermore, the most hydrophobic of the cubic phase particles, namely that with the low level of sodium oleate as the dispersant, binds the most among the cubic phase formulations, whereas the lowest binding is seen with the "stealth" particle with a PEGylated surfactant (Pluronic F68) as the dispersant.

The propofol (1%) in each of these dispersions produces a reasonable representation of what the particle chemistry might look like after absorbing propofol, a potential application of the invention as exemplified in Example 18, and this electrophoresis measurement demonstrates that the plasma protein binding of reversed cubic phase particles of the invention in such an application can be modulated by manipulating the composition of the particle. This can be used to influence the distribution and clearance of particles in the application of the invention, and may allow optimization of the particles with respect to opsonization, targeting, and minimal disruption of physiological processes.

Example 10

The uptake of 3 toxins-paraoxon, etomidate, and clomipramine—into particles of the invention, in the presence of albumin, was measured in this Example. Two dispersions, one at approximately 5.6 vol % particle concentration and the other approximately 15%, were prepared as follows. An amount 1.4195 gm of sodium deoxycholate was dissolved in 14.5705 gm of sterile water for injection, to which were added 10.1382 gm of alpha-tocopherol and 23.8061 gm of phosphatidylcholine (Phospholipon 90G from Phospholipid GmbH), and the mixture was stirred vigorously. From this, 35.66 gm were combined with 707.42 gm of sterile water for injection, and the mixture homogenized at 5200 RPM with a Silverson AX60 ½ HP homogenizer at ambient temperature, with temperature maintained below 26° C. by ice water jacketing. After 75 minutes, 7.237 gm of tocopherol were slowly dripped in to the dispersion. Homogenization continued until the particle size was such that the dispersion could be filtered through a 2 micron depth filter, follow by a 1.2 micron membrane filter. This dispersion was then split in half, and to one half was added 8.07 gm of glycine, and sufficient NaOH to yield a pH of 7.6. The other half of the dispersion was placed in a round bottom flask and on a rotovap, whereupon the dispersion weight was reduced from 344.3 gm to 119.9 gm; 2.604 gm of glycine and sufficient NaOH were added to yield a final pH of 7.7. Twenty-milliliter vials were filled, sparged and autoclaved at 121° for 20 minutes, yielding two sterile dispersions, which will be referred to as "RA5-5E" and "RA5-15E" for the 5.6% and 15% particle concentrations, respectively. The zeta potentials were recorded as −46 mV and −32 mV, respectively.

Three toxin solutions were prepared. These were: 18 mg of etomidate in 9 mL of Krebbs-Ringer buffer with 40 mg/mL albumin, 20 microliters of paraoxon in 10 mL deionized water, and 15.1 mg of clomipramine in 30 mL of Krebbs-Ringer buffer with albumin.

Nanosep Omega centrifuge filters at 300,000 MWCO from Pall Filtron were used to separate particles from exterior phase. Thus, into each filter tube were placed 50 microliters of either RA5-5E or RA5-15E (also called LT-728(5E) and LT-728(15E) respectively), 100 microliters of toxin solution, and 150 microliters of distilled water. The loaded tubes were incubated at 40° C. for 45 minutes, then centrifuged at 10,800 RPM in a Jouan high-speed centrifuge for approximately 1 hour.

For HPLC analysis, the bottom phase liquid (filtrate) was injected directly, and the top phase (retentate) dissolved in 500 microliters of methanol, then injected. The mobile phase in the HPLC was 30% pH 8.1 phosphate buffer, 35% acetonitrile and 35% methanol. Standards were run for each of the toxins, and toxin concentrations determined in the exterior (bottom) phase and in the top phase retentate.

The following three tables show the data (assay values are in mg/mL) and the analysis thereof, for the three toxins. The analysis proceeded as follows. The top phase dilution factor was first computed by noting that either 5.6 or 14% liquid crystal was diluted into 500 microliters of methanol. From this and the top phase assay value, the concentration of toxin in the particles was back-calculated. This was then divided by the aqueous phase (bottom phase) concentration, since this was undiluted, in order to arrive at an effective partition coefficient. To check the validity of the calculation, a mass balance was performed by properly combining the two concentrations and respective volumes, and checking how close the result comes to the target, or theoretical, value, which is 50.3 in the clomipramine case and 200 in the other two cases (reflecting the 4-fold lower toxin concentration in the clomipramine toxin solution). One skilled in the art will recognize that this calculation is designed such that errors due to incomplete separation of exterior phase from the particles are minimized—in particular, by using the known particle concentration rather than a measured top phase volume, the need for complete particle separation is circumvented.

| CLOMIPRAMINE | | | | | |
|---|---|---|---|---|---|
| | Assay | Particle concn | Top ph dilution | Eff part coefficient | Drug acct (target = 50.3) |
| Bottom phase | | | | | |
| LT-728 (5E) | 0.00562 | 0.056 | 179.6 | 3195.2 | 52.0 |
| LT-728 (15E) | 0.00288 | 0.15 | 67.7 | 2348.6 | 51.6 |
| Top phase | | | | | |
| LT-728 (5E) | 0.1 | | | | |
| LT-728 (15E) | 0.09996 | | | | |

| PARAOXON | | | | | |
|---|---|---|---|---|---|
| | Assay | Particle concn | Top ph dilution | Eff part coefficient | Bup acct (target = 200) |
| Bottom phase | | | | | |
| LT-728 (5E) | 0.462 | 0.056 | 179.6 | 81.6 | 242.9 |
| LT-728 (15E) | 0.207 | 0.15 | 67.7 | 98.4 | 213.3 |
| Top phase | | | | | |
| LT-728 (5E) | 0.21 | | | | |
| LT-728 (15E) | 0.301 | | | | |

| ETOMIDATE | | | | | |
|---|---|---|---|---|---|
| | Assay | Particle concn | Top ph dilution | Eff part coefficient | Etom acct (target = 200) |
| Bottom phase | | | | | |
| LT-728 (5E) | 0.257 | 0.056 | 179.6 | 129.3 | 169.4 |
| LT-728 (15E) | 0.148 | 0.15 | 67.7 | 136.7 | 195.0 |
| Top phase | | | | | |
| LT-728 (5E) | 0.185 | | | | |
| LT-728 (15E) | 0.299 | | | | |

Thus the experiment demonstrates that etomidate and paraoxon, and particularly clomipramine, partitioned strongly into the particles of the invention in this experiment. This is true even though the experiments were performed in the presence of albumin, which of course greatly increases the solubility of the toxins in water, and thus yields a much lower value for the effective partition coefficient than would be found for the true partition coefficient, that is, without albumin. Indeed, albumin was included in order to more closely simulate conditions under which the invention will be used. When the experiment was repeated with etomidate in the absence of albumin, an effective partition coefficient of 309 was recorded (with the mass balance within 5% of theoretical).

Example 11

Using the same dispersions and methods as in Example 10, the effective partition coefficients of lidocaine, benzocaine, and bupivacaine in the presence of albumin were measured. Lidocaine yielded a value of 57 (with the mass balance being within 3% of theoretical), benzocaine a value of 148 (with the mass balance being 84 whereas 95 was theoretical), in the case of the RA5-15E dispersion, and the value for bupivacaine was 62 (mass balance within 3% of theoretical).

Example 12

In this Example, strontium ions ($Sr^{2+}$), which are known in the art to bind to phosphatidylcholine head groups, were shown to exhibit strong binding to the bilayer-rich cubic phase particles of the invention. To demonstrate this, 18.9 mM of strontium chloride was added to an aliquot of the "RA5-15E" dispersion of the invention prepared in Example 10. A high degree of binding of strontium ions to the phosphatidylcholine in RA5-15E was evidenced by the immediate precipitation of the cubic phase, which centrifuged to the bottom of the dispersion. Were the heavy strontium ions not bound, the cubic phase would be less dense than water and would have centrifuged to the top of the dispersion, as is the usual case with other methods of precipitating the particles. Radiostrontium, and to a lesser extent strontium, have known toxic effects, as do related phosphatidylcholine-binding metals. More broadly, this Example illustrates how the effect of large bilayer surface areas in cubic phase particles can result in effective uptake of toxins that bind to bilayer components.

Example 13

A 15% particle concentration dispersion of the invention was made in the Example without requiring rotovapping (as was used in Example 10). An amount 1.9093 gm of sodium deoxycholate was dissolved in 24.761 gm of sterile water for injection, to which were added 15.94 gm of alpha-tocopherol and 24.06 gm of phosphatidylcholine (Phospholipon 90G from Phospholipid GmbH), and the mixture was stirred vigorously. From this, 60.01 gm were combined with 554.99 gm of sterile water for injection plus 2.00 mL of 1N NaOH, and the mixture homogenized at 5200 RPM with a Silverson AX60 ½ P homogenizer at ambient temperature, with temperature maintained between 19° and 28° C. by ice water jacketing. After 3 hours, 3.6999 gm of tocopherol were slowly dripped in to the dispersion. Homogenization continued for 2 hours and 20 minutes. Glycerol was added to a concentration of 2.3% for tonicity, the dispersion filtered through a 2 micron depth filter, and phosphate buffer added to a concentration of 20 mM, and the pH adjusted. Vials were loaded, sparged with nitrogen, capped and autoclaved at 121° C. and 15 psi for 15 minutes. The final dispersion had a mean particle size, using unimodal analysis, of 193 nm, and a pH of 8.0.

Example 14

In this Example a fluorocarbon was incorporated into the particles, making the particles well suited for uptake of diatomic nitrogen, for potential treatment or prophylaxis of decompression sickness ("the bends" and related conditions). The specific fluorocarbon used was hexafluoropropanol. To start, 0.318 gm of sodium deoxycholate was dissolved in 4.127 gm of water. To this were added 4.01 gm of soy phosphatidylcholine (Lipoid E80), 1.96 gm of alpha-tocopherol, and 0.960 gm of hexafluoropropanol. Mixing this created a high-viscosity reversed cubic phase. An amount 10.16 gm of this liquid crystal was combined with 94.94 gm of water and 1.837 gm of glycerol (for tonicity), and the mixture homogenized with an Intron lab-scale homogenizer. The result was a fine dispersion of the invention, with approximately 10% fluorocarbon in the cubic phase, or phrased otherwise, where approximately 17% of the bilayer in the cubic phase was fluorocarbon.

Example 15

In this Example, the partitioning of the quaternary ammonium skeletal muscle relaxant vecuronium bromide, a water-soluble compound with a low octanol-water partition coefficient, between a phosphatidylcholine/tocopherol/water reversed cubic phase and water is measured, and found to be very high, sufficiently high as to enable the use of the invention in attenuating the effect of the drug in the body of a mammal. An amount 0.6169 gm of phosphatidylcholine (Phospholipon 90G, from Phospholipid GmbH) was mixed with 0.6730 gm of alpha-tocopherol and 0.2194 gm of a 10% vecuronium bromide solution in water. An amount 1.1226 gm of this mixture was smeared onto the inner wall of a test tube, and 6.4495 gm of water added to the tube so as to contact the mixture. Upon swelling with water, the mixture became a reversed cubic phase. After 3 days of contact between the cubic and aqueous phases to allow equilibration of the drug between the two phases, HPLC analysis showed that the concentration of vecuronium in the cubic phase was 10.0 mg/mL, while that in the aqueous phase was only 0.006 mg/mL. The partition coefficient between cubic phase and water was thus approximately 1,600 (or log $K_{OW}$=3.2). When the content of anionic lipid was increased significantly by incorporating a bile salt, this increased to log $K_{OW}$ approximately 4, which could reflect additional binding of drug due to electrostatic interactions with the bilayer-bound anion. One with ordinary skill in the art will recognize that the vecuronium mass balance checks correctly if one assumes that the water content of the final cubic phase, after swelling to equilibrium, is approximately 40%, which is in perfect accord with the phase diagram derived in this laboratory for this cubic phase region.

Example 16

The RA5-5E and RA5-15E dispersions prepared in Example 10 were tested in vivo as prophylaxis, in a rat model incorporating a normally-lethal intravenous injection of bupivacaine. Sixteen adult male rats were randomly arranged into four groups of four animals each. Each group of animals were pre-treated with intravenous doses of either 4 ml/Kg normal physiologic saline (Group A), 4 ml/Kg of dispersion RA5-15E of the instant invention with a 15 percent particle concentration (Group B), 6 ml/Kg of dispersion RA5-5E of the instant invention with a 5.6 percent particle concentration (Group C) or 4 ml/Kg Intralipid®, a commercially available fat emulsion useful for parenteral nutrition. Animals in all four groups were then given intravenously a known lethal dose (12 mg/Kg) of the amide local anesthetic bupivacaine. Animals from each group were then monitored for signs and symptoms of cardiotoxicity resulting from the administration of bupivacaine. All four animals in Group A became pulseless within 10 seconds of the injection of bupivacaine while all of the animals in the remaining three groups survived without clinical signs of cardiotoxicity. This example demonstrates the use of the invention as prophylaxis to toxic injury.

Example 17

The RA5-5E and RA5-15E dispersions prepared in Example 10 were subsequently tested in vivo as a rescue agent in a rat model incorporating a normally-lethal intravenous injection of bupivacaine. Twelve adult male rats were randomly arranged into three groups of four animals each. Animals in each group were given a known lethal dose (12 mg/Kg) of the amide local anesthetic bupivacaine intravenously. Each animal was monitored for signs of acute cardiotoxicity. All animals became pulseless within 10 seconds of the injection of bupivacaine. When each animal became pulseless, it was treated immediately with mild chest compression and with one of the following: (i) 4 ml/Kg normal physiologic saline (Group A); (ii) 4 ml/Kg of dispersion RA5-15E of the instant invention with a 15 percent particle concentration (Group B); or, (iii) 6 ml/Kg of dispersion RA5-5E of the instant invention with a 5.6 percent particle concentration (Group C). All four animals in Group A succumbed, while all four animals in Groups B and C recovered and exhibited normal pulse within minutes of administration of the dispersion of the instant invention. The administration of the dispersion according to the instant invention rescued the animals from death due to the systemic toxicity of an overdose of a common local anesthetic agent.

Example 18

Ten adult rats with previously inserted in-dwelling intra-jugular (IJ) venous cannulae were given 10 mg/kg of the intravenous anesthetic induction agent, propofol, via the indwelling IJ catheter. This constitutes a therapeutic dose. The Time to Emergence from anesthesia (defined as the elapsed time from the start of the propofol injection until the time of eye-closure and the loss of palpebral or eyelash reflex) was recorded for each of the animals.

Twenty four hours later, the same group of ten animals was again given the same dose of 10 mg/kg of propofol via the indwelling IJ catheter. Immediately after induction of anesthesia, each animal was given an IJ injection of dispersion RA5-15E from Example 10, at 4 ml/Kg. The Time to Emergence from anesthesia was recorded as on Day 1 for each animal. The differences in Time to Emergence from Day 1 to Day 2 calculated for each animal. The Time to Emergence from anesthesia was less for every one of the ten animals on Day 2 than on Day 1. The mean reduction in Time to Emergence from Day 1 to Day 2 was 23%, with a minimum reduction of 13% and a maximum reduction of 37%. The administration of the dispersion decreased the Time to Emergence, in this way attenuating the therapeutic effect of a therapeutic dose of the common general anesthetic propofol.

Example 19

Amphotericin B provides an example of an API with high toxicity which has a site of action in the interior of a fungal lipid biomembrane. In this Example the partition coefficient of amphotericin B between the preferred cubic phase of the invention (composition approximately 30% phosphatidylcholine, 30% alpha-tocopherol and 40% water) and water (both phases containing residual DMSO from the experiment) was measured using HPLC, and this partition coefficient was found to be approximately 1,000.

An amount 0.0082 g of Amphotericin B and 0.8 mL of DMSO (dimethylsulfoxide) were added to a 16 mL test tube. The test tube was heated to 60° C. until the amphotericin B was completely dissolved. An amount 0.692 g of 2.5% DMPG in the phosphatidylcholine product Lipoid E80, 0.8 mL of DMSO, and 0.6 mL of ethanol were added to a second 16 mL test tube. The mixture was heated to 60° C. and vortexed until the Lipoid E80/DMPG was entirely dissolved. An amount 0.6873 g of vitamin E and 0.8 mL of DMSO were added to a third 16 mL test tube. The mixture was heated to 60° C. and vortexed until the vitamin E was completely dissolved. The contents of the second and third test tubes were added to the first test tube containing the amphotericin B and DMSO mixture. The test tube containing the entire mixture was heated to 60° C. for 30 minutes to ensure that all components were completely dissolved.

An amount of 10 mL of deionized water was added to the test tube. The test tube was gently shaken at 40 RPM for 30 minutes on a Lab-Line Junior Orbit Shaker. The aqueous portion was decanted and filtered through Aldrich medium speed filter paper into a clean test tube and labeled "wash 1". This washing procedure was repeated three additional times to obtain "wash 2", "wash 3", and "wash 4".

HPLC analysis was then performed to determine the amphotericin B concentrations in the 4 wash solutions and the final, quadruply-washed cubic phase. The latter concentration was found to be 1.76 mg/mL, and it was ascertained that the cubic phase contained entrapped pockets of water (as evidenced by an opaque appearance, for example), so that the true concentration in the cubic phase itself was estimated to be approximately 3 mg/mL. In contrast, the amphotericin B concentrations in the "wash 3" and "wash 4" solutions were both approximately 0.0035 mg/mL, thus making the partition coefficient on the order of 1,000.

It is known that amphotericin B partitions much more strongly into fungal cell membranes, the site of pharmacologic action, than into cell membranes of the human kidney, the site of toxic action. It is therefore possible that the application of the instant invention, using for example a phospholipid/tocopherol/water composition, could recover amphotericin B from the site of toxic action preferentially over the site of desirable pharmacologic action, thus increasing the therapeutic index, or relieving a patient of toxic effects while maintaining antifungal activity.

We claim:

1. A method of absorbing or adsorbing one or more compounds in vivo, comprising the steps of:
    identifying a patient who has or is suspected of having said one or more compounds in said patient's tissues or blood stream, said one or more compounds being selected from a drug, toxin, or exogenous or endogenous substance which satisfies one or more of the following criteria
        a) contiguous string or ring of at least six carbon atoms,
        b) solubility of at least 1% in alpha-tocopherol,
        c) an octanol-water partition coefficient equal to or greater than 100,
        d) lowers surface tension of water to less than 50 dynes/cm at concentrations of 1% or less, or
        e) contains a contiguous sequence of at least four hydrophobic amino acids;
    administering to said patient a liquid composition comprising particles stabilized in dispersion in a polar solvent, said particles consisting essentially of reversed cubic phase or reversed hexagonal phase material; and
    using said particles to absorb or adsorb said one or more compounds by solubilization or partitioning of said one or more compounds into said reversed cubic phase or reversed hexagonal phase material.

2. The method of claim 1 wherein said particles are uncoated and ionically charged.

3. The method of claim 1 wherein said reversed cubic phase or reversed hexagonal phase material is comprised of (i) a lipid or surfactant, (ii) a polar solvent, and (iii) one or more hydrophobes selected from the group consisting of tocopherol, linalool, and benzyl benzoate.

4. The method of claim 1 wherein said reversed cubic phase or reversed hexagonal phase material comprises phosphatidylcholine and tocopherol.

5. The method of claim 1 wherein said particles have an average particle size ranging from 40 nm to 1000 nm in size.

6. The method of claim 1, wherein said one or more compounds is selected from: anesthetics, opiates, analgesics, benzodiazepines, hypnotics and barbiturates.

7. The method of claim 1, wherein said one or more compounds includes at least one anesthetic that is a local anesthetic selected from bupivacaine, lidocaine, procaine, tetracaine, mepivacaine, etidocaine, oxybuprocaine, cocaine, benzocaine, pramixinine, prilocaine, proparacaine, ropivicaines, chloroprocaine, and dibucaine.

8. The method of claim 7, wherein said local anesthetic is bupivacaine.

9. The method of claim 7, wherein said local anesthetic is cocaine.

10. The method of claim 1, wherein said one or more compounds includes at least one anesthetic that is a general anesthetic selected from propofol, alphaxalone, alfatalone, alphadolone, eltanolone, propanidid, ketamine, pregnanolone, and etomidate.

11. The method of claim 10, wherein said general anesthetic is propofol.

12. The method of claim 1, wherein said one or more compounds includes at least one toxin.

13. The method of claim 1 wherein said step of identifying includes the step of administering said one or more compounds to said patient.

14. The method of claim 4 wherein the particles further comprise water and one or more stabilizers.

15. The method of claim 14 wherein said one or more stabilizers include bile salts.

16. The method of claim 1 wherein the liquid composition consists essentially of phosphatidylcholine, alpha tocopherol, water, one or more stabilizers, one or more tonicity adjustors, and one or more buffers.

17. The method of claim 1 wherein said one or more compounds is a drug.

* * * * *